US012198809B2

(12) United States Patent
Evans et al.

(10) Patent No.: US 12,198,809 B2
(45) Date of Patent: *Jan. 14, 2025

(54) MACHINE LEARNING ALGORITHMS FOR DETECTING MEDICAL CONDITIONS, RELATED SYSTEMS, AND RELATED METHODS

(71) Applicants: Neil Reza Shadbeh Evans, Peoria, IL (US); Nick Shadbeh Evans, Lynnwood, WA (US)

(72) Inventors: Neil Reza Shadbeh Evans, Peoria, IL (US); Nick Shadbeh Evans, Lynnwood, WA (US)

( * ) Notice: Subject to any disclaimer, the term of this patent is extended or adjusted under 35 U.S.C. 154(b) by 803 days.

This patent is subject to a terminal disclaimer.

(21) Appl. No.: 17/318,347

(22) Filed: May 12, 2021

(65) Prior Publication Data

US 2021/0398655 A1 Dec. 23, 2021

Related U.S. Application Data

(60) Provisional application No. 63/041,527, filed on Jun. 19, 2020.

(51) Int. Cl.
*G16H 50/20* (2018.01)
*A61B 5/00* (2006.01)
(Continued)

(52) U.S. Cl.
CPC .......... *G16H 50/20* (2018.01); *A61B 5/0205* (2013.01); *A61B 5/021* (2013.01); *A61B 5/024* (2013.01);
(Continued)

(58) Field of Classification Search
CPC ........ G16H 50/20; G16H 10/60; G16H 50/70; G16H 10/20; G16H 30/40; G16H 30/20;
(Continued)

(56) References Cited

U.S. PATENT DOCUMENTS 8,296,247 B2 10/2012 Zhang et al.
8,379,970 B2 2/2013 Woo et al.
(Continued)

FOREIGN PATENT DOCUMENTS

CN 107967941 A 4/2018
CN 106372390 B 4/2019
(Continued)

OTHER PUBLICATIONS

English-language machine translation of abstract of Chinese Patent No. CN 106372390 B, Apr. 2, 2019.
(Continued)

*Primary Examiner* — John J Lee
(74) *Attorney, Agent, or Firm* — Kolitch Romano Dascenzo Gates LLC

(57) ABSTRACT

Systems for preparing, training, and deploying a machine learning algorithm for making medical condition state determinations include at least one processing unit that includes the machine learning algorithm. The at least one processing unit is programmed to receive image input from an imaging device, receive patient health data, encode the patient health data to convert the patient health data to encoded patient health data, and transmit the encoded patient health data into the machine learning algorithm. Systems are configured to make a medical condition state determination based on the image input and the encoded patient health data, via the machine learning algorithm, and provide visual output for the medical condition state determination via a display device such that the visual output may be augmented with the patient health data. Dynamic state information also may be input to the machine learning algorithm and used to make medical condition state determinations.

30 Claims, 15 Drawing Sheets

(51) Int. Cl.

| | |
|---|---|
| *A61B 5/0205* | (2006.01) |
| *A61B 5/021* | (2006.01) |
| *A61B 5/024* | (2006.01) |
| *A61B 5/08* | (2006.01) |
| *A61B 5/083* | (2006.01) |
| *A61B 5/145* | (2006.01) |
| *G06N 20/00* | (2019.01) |
| *G06Q 30/04* | (2012.01) |
| *G06T 7/00* | (2017.01) |
| *G16H 10/20* | (2018.01) |
| *G16H 10/60* | (2018.01) |
| *G16H 15/00* | (2018.01) |
| *G16H 30/20* | (2018.01) |
| *G16H 30/40* | (2018.01) |
| *G16H 50/50* | (2018.01) |
| *G16H 50/70* | (2018.01) |

(52) U.S. Cl.
 CPC .......... *A61B 5/0816* (2013.01); *A61B 5/0836* (2013.01); *A61B 5/14542* (2013.01); *A61B 5/7267* (2013.01); *G06N 20/00* (2019.01); *G06Q 30/04* (2013.01); *G06T 7/0012* (2013.01); *G16H 10/20* (2018.01); *G16H 10/60* (2018.01); *G16H 15/00* (2018.01); *G16H 30/20* (2018.01); *G16H 30/40* (2018.01); *G16H 50/50* (2018.01); *G16H 50/70* (2018.01); *G06T 2207/20081* (2013.01); *G06T 2207/20084* (2013.01); *G06T 2207/30048* (2013.01)

(58) Field of Classification Search
 CPC ...... G16H 50/50; G16H 15/00; G06T 7/0012; G06T 2207/20081; G06T 2207/20084; G06T 2207/30048; G06N 20/00; A61B 5/0205; A61B 5/021; A61B 5/024; A61B 5/0816; A61B 5/0836; A61B 5/14542; A61B 5/7267; G06Q 30/04
 See application file for complete search history.

(56) References Cited

U.S. PATENT DOCUMENTS

| | | | |
|---|---|---|---|
| 9,798,918 | B2 | 10/2017 | Remiszewski et al. |
| 10,360,675 | B2 | 7/2019 | Reicher et al. |
| 10,855,957 | B2 | 12/2020 | Kapoustin et al. |
| 2009/0136111 | A1 | 5/2009 | Jabri et al. |
| 2012/0185275 | A1* | 7/2012 | Loghmani .............. G06Q 40/08 705/3 |
| 2014/0286561 | A1 | 9/2014 | Remiszewski et al. |
| 2015/0133785 | A1 | 5/2015 | Schlenger |
| 2016/0125135 | A1 | 5/2016 | Ramanthan et al. |
| 2016/0203263 | A1 | 7/2016 | Maier et al. |
| 2016/0224750 | A1 | 8/2016 | Kethman et al. |
| 2016/0364631 | A1 | 12/2016 | Reicher et al. |
| 2016/0364857 | A1 | 12/2016 | Reicher et al. |
| 2017/0358078 | A1* | 12/2017 | Hoff ...................... G06T 7/0012 |
| 2018/0241563 | A1* | 8/2018 | Benchetrit .............. G06F 16/41 |
| 2019/0392943 | A1 | 12/2019 | Sorenson et al. |
| 2020/0051696 | A1 | 2/2020 | Zhao et al. |
| 2020/0134276 | A1 | 4/2020 | Hazan |
| 2020/0193597 | A1 | 7/2020 | Fan et al. |
| 2021/0344880 | A1 | 11/2021 | Katra et al. |
| 2022/0351838 | A1 | 11/2022 | Pedemonte et al. |
| 2023/0181042 | A1 | 6/2023 | Fan et al. |
| 2023/0222654 | A1* | 7/2023 | Fan ........................ A61B 5/445 382/128 |

FOREIGN PATENT DOCUMENTS

| | | |
|---|---|---|
| DE | 102010006991 A1 | 8/2011 |
| KR | 102058883 B1 | 12/2019 |
| WO | WO 2017/027475 A1 | 2/2017 |
| WO | WO 2019/200535 A1 | 10/2019 |

OTHER PUBLICATIONS

English-language machine translation of abstract of Chinese Patent Application Publication No. CN 107967941 A, Apr. 27, 2018.

English-language machine translation of description of German Patent Application Publication No. DE 102010006991 A1, Aug. 11, 2011.

English-language machine translation of abstract of Korean Patent No. KR 102058883 B1, Dec. 24, 2019.

English-language machine translation of description of PCT Patent Application Publication No. WO 2019200535 A1, Oct. 24, 2019.

Abadir et al., "Artificial Intelligence in Gastrointestinal Endoscopy", Focused Review Series: Application of Artificial Intelligence in GI Endoscopy, Clin Endosc. 2020;53 (2): 132-141. doi:https://doi.org/10.5946/ce.2020.038.

Ahmed et al., "Artificial intelligence with multi-functional machine learning platform development for better healthcare and precision medicine", Database, vol. 2020, 2020, baaa010. https://doi.org/10.1093/database/baaa010.

Alagappan et al., "Artificial intelligence in gastrointestinal endoscopy: The future is almost here", World J Gastrointest Endosc 2018; 10(10): 239-249. https://dx.doi.org/10.4253/wjge.v10.i10.239.

Aziz et al., "The impact of deep convolutional neural network-based artificial intelligence on colonoscopy outcomes: a systematic review with meta-analysis", Journal of gastroenterology and hepatology vol. 35,10 (2020): 1676-1683. doi:10.1111/jgh.15070.

Boroff et al., "Adenoma and Polyp Detection Rates in Colonoscopy according to Indication", Gastroenterology Research and Practice, vol. 2017, Article ID 7207595, 6 pages, 2017. https://doi.org/10.1155/2017/7207595.

Byrne et al. "Real-time differentiation of adenomatous and hyperplastic diminutive colorectal polyps during analysis of unaltered videos of standard colonoscopy using a deep learning model", Gut. 68. gutjnl-2017 (2017). 10.1136/gutjnl-2017-314547.

Crockett et al., "Terminology, Molecular Features, Epidemiology, and Management of Serrated Colorectal Neoplasia", Gastroenterology, vol. 157, Issue 4, 949-966.e4. https://doi.org/10.1053/j.gastro.2019.06.041.

Hilsden et al., "Prediction of findings at screening colonoscopy using a machine learning algorithm based on complete blood counts (ColonFlag)." PloS one 13.11 (2018): e0207848. https://doi.org/10.1371/journal.pone.0207848.

Howard et al,. "MobileNets: Efficient Convolutional Neural Networks for Mobile Vision Applications." ArXiv abs/1704.04861 (2017): n. pag.

Ker et al., "Deep Learning Applications in Medical Image Analysis," in IEEE Access, vol. 6, pp. 9375-9389, 2018, doi: 10.1109/ACCESS.2017.2788044.

Kobayashi et al., "Diagnostic yield of the Japan NBI Expert Team (JNET) classification for endoscopic diagnosis of superficial colorectal neoplasms in a large-scale clinical practice database", UEG Journal, 7: 914-923 (2019). https://doi.org/10.1177/2050640619845987.

Le Berre et al., "Application of Artificial Intelligence to Gastroenterology and Hepatology", Reviews and Perspectives Reviews in Basic and Clinical Gastroenterology and Hepatology, vol. 158, Issue 1, p. 76-94.E2, 2019. https://doi.org/10.1053/j.gastro.2019.08.058.

Mori et al., "Cost savings in colonoscopy with artificial intelligence-aided polyp diagnosis: an add-on analysis of a clinical trial (with video)", Gastrointestinal Endoscopy (2020), doi: https://doi.org/10.1016/j.gie.2020.03.3759.

Mori et al., "Detecting colorectal polyps via machine learning", Nat Biomed Eng 2, 713-714 (2018). https://doi.org/10.1038/s41551-018-0308-9.

(56) References Cited

OTHER PUBLICATIONS

Ozawa et al. "Automated Endoscopic Detection and Classification of Colorectal Polyps Using Convolutional Neural Networks." Therapeutic Advances in Gastroenterology, Jan. 2020, doi:10.1177/1756284820910659.

Puig et al., "Optical Diagnosis for Colorectal Polyps: a Useful Technique Now or in the Future?", Gut Liver. Jul. 15, 2018;12(4):385-392. doi: 10.5009/gnl17137.

Sánchez-Montes et al., "Computer-aided prediction of polyp histology on white light colonoscopy using surface pattern analysis", Endoscopy 2019; 51(03): 219-220. doi: 10.1055/a-0754-5556.

Song et al., "Volumetric texture features from higher-order images for diagnosis of colon lesions via CT colonography", International journal of computer assisted radiology and surgery vol. 9,6 (2014): 1021-31. doi:10.1007/s11548-014-0991-2.

Szegedy et al., "Rethinking the Inception Architecture for Computer Vision." 2016 IEEE Conference on Computer Vision and Pattern Recognition (CVPR) (2016): 2818-2826. arXiv:1512.00567.

Urban et al., "Deep Learning Localizes and Identifies Polyps in Real Time With 96% Accuracy in Screening Colonoscopy", Gastroenterology, vol. 155, Issue 4, 2018, pp. 1069-1078.e8, ISSN 0016-5085, https://doi.org/10.1053/j.gastro.2018.06.037.

Wan et al., "An Early Intestinal Cancer Prediction Algorithm Based on Deep Belief Network", Sci Rep 9, 17418 (2019). https://doi.org/10.1038/s41598-019-54031-2.

Wang et al., "Development and validation of a deep-learning algorithm for the detection of polyps during colonoscopy", Nat Biomed Eng 2, 741-748 (2018). https://doi.org/10.1038/s41551-018-0301-3.

Willemink et al., "Preparing Medical Imaging Data for Machine Learning", Radiology 2020 295:1, 4-15. https://doi.org/10.1148/radiol.2020192224.

Yamada et al., "Development of a real-time endoscopic image diagnosis support system using deep learning technology in colonoscopy", Sci Rep 9, 14465 (2019). https://doi.org/10.1038/s41598-019-50567-5.

* cited by examiner

MACHINE LEARNING ALGORITHMS FOR DETECTING MEDICAL CONDITIONS, RELATED SYSTEMS, AND RELATED METHODS

RELATED APPLICATION

This application claims priority to U.S. Provisional Patent Application No. 63/041,527, filed on Jun. 19, 2020, and entitled MACHINE LEARNING MODEL FOR DETECTING MEDICAL CONDITIONS.

FIELD

The present disclosure relates generally to machine learning algorithms for detecting medical conditions, and more particularly to machine learning algorithms, systems, and methods for real-time analysis of medical images from medical imaging procedures.

BACKGROUND

Medical imaging is widely used for screening and diagnosis of a wide variety of medical conditions, and may include techniques such as sonography videos, x-ray films, computed tomography (CT) scans, magnetic resonance imaging (MRI) scans, positron emission tomography (PET) scans, retinal photography, histology slides, dermoscopy images, radiography, mammography, as well as laparoscopic videos, endoscopic techniques, including lower endoscopy (e.g., colonoscopy), upper endoscopy (e.g., esophagogastroduodenoscopy), bronchoscopy, and capsule endoscopy procedures (e.g., Pillcam™) for examining the entire digestive system. Such visual inspections can be used in screening or diagnosing cancer, lesions, auto-immune diseases, infections, and many other medical conditions. Images (or in some cases, videos) produced via these and other medical imaging procedures can be too numerous for examining physicians to individually analyze each image. Artificial intelligence is thus increasingly utilized in analyzing and interpreting images from medical imaging procedures.

For example, machine learning models such as convolutional neural networks (CNNs) have been trained to analyze medical images and perform classification and diagnoses of various conditions. Such models have been trained using datasets having a feature of interest and datasets that do not include the feature to "learn" a function. Once the model is trained and validated, it can then be used to make determinations on new data/inputs, and thus aid health care workers in medical image analysis. In a specific example, CNNs have been trained to detect and localize a lesion in a colonoscopy procedure. While such models have improved in accuracy in recent years, many remain limited in the speed at which they can analyze medical images. Existing models also are limited in their ability to present visualization of data from multiple data sources to the examining physician, in their training methods, and/or in their ability to receive larger image datasets for analysis.

SUMMARY

Presently disclosed systems for preparing, training, and deploying a machine learning algorithm for medical condition state determination include at least one processing unit comprising the machine learning algorithm. The at least one processing unit may be programmed to receive an image input, receive patient health data as input, encode the patient health data to convert the patient health data to encoded patient health data, transmit the encoded patient health data into the machine learning algorithm, and make a medical condition state determination based on the image input and the encoded patient health data, via the machine learning algorithm. The image input generally includes one or more images from an imaging device, such as from a colonoscopy or other medical imaging procedure.

Presently disclosed methods of training and preparing a machine learning algorithm for medical condition state determination may include acquiring data from at least one medical procedure. For example, acquiring data may include acquiring at least one in situ biological image of an area of a body of a patient and/or acquiring one or more biological specimens from the area. Methods also may include labeling the at least one in situ biological image, thereby creating at least one labeled biological image that indicates respective medical condition states shown in each respective biological image, acquiring patient health data pertaining to the patient from a plurality of data sources, and aggregating the patient health data acquired from the plurality of data sources into a database (e.g., a text-based or other form of database). The patient health data in the database may be de-identified in some methods. In this manner, methods may include training the machine learning algorithm using the data from the database and the at least one labeled biological image.

In other presently disclosed methods of training and preparing a machine learning algorithm for making a medical condition state determination, the method may include receiving an image input via at least one processing unit, wherein the image input comprises one or more images from an imaging device, and wherein the at least one processing unit comprises a machine learning algorithm, and receiving patient health data as input, wherein the receiving patient health data is performed by the at least one processing unit. Such methods may further include encoding the patient health data and thereby converting the patient health data to encoded patient health data, wherein the encoding the patient health data and the converting the patient health data is performed by the at least one processing unit. Disclosed methods also may include embedding the encoded patient health data into at least one image of the image input, wherein the embedding the encoded patient health data is performed by the at least one processing unit, wherein the machine learning algorithm is configured to make the medical condition state determination based on the image input and the encoded patient health data. Other related systems and methods also are disclosed, along with the machine learning algorithms themselves.

DESCRIPTION

Systems according to the present disclosure may be used to prepare, train, and deploy machine learning algorithms for medical condition state determinations.

Figure 1:
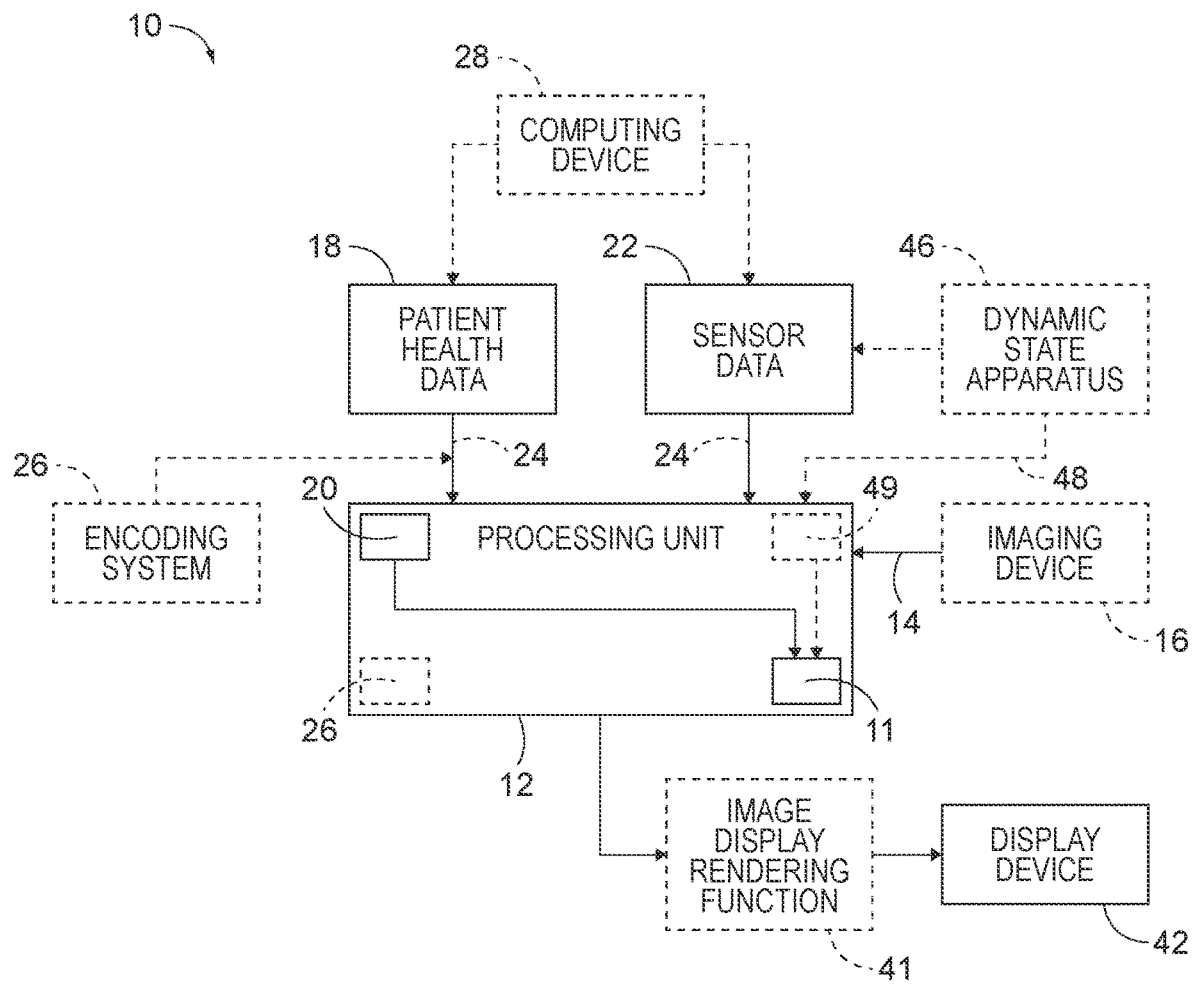
FIG. 1 is a schematic representation of non-exclusive examples of systems for detecting medical conditions, according to the present disclosure.
Figure 2:
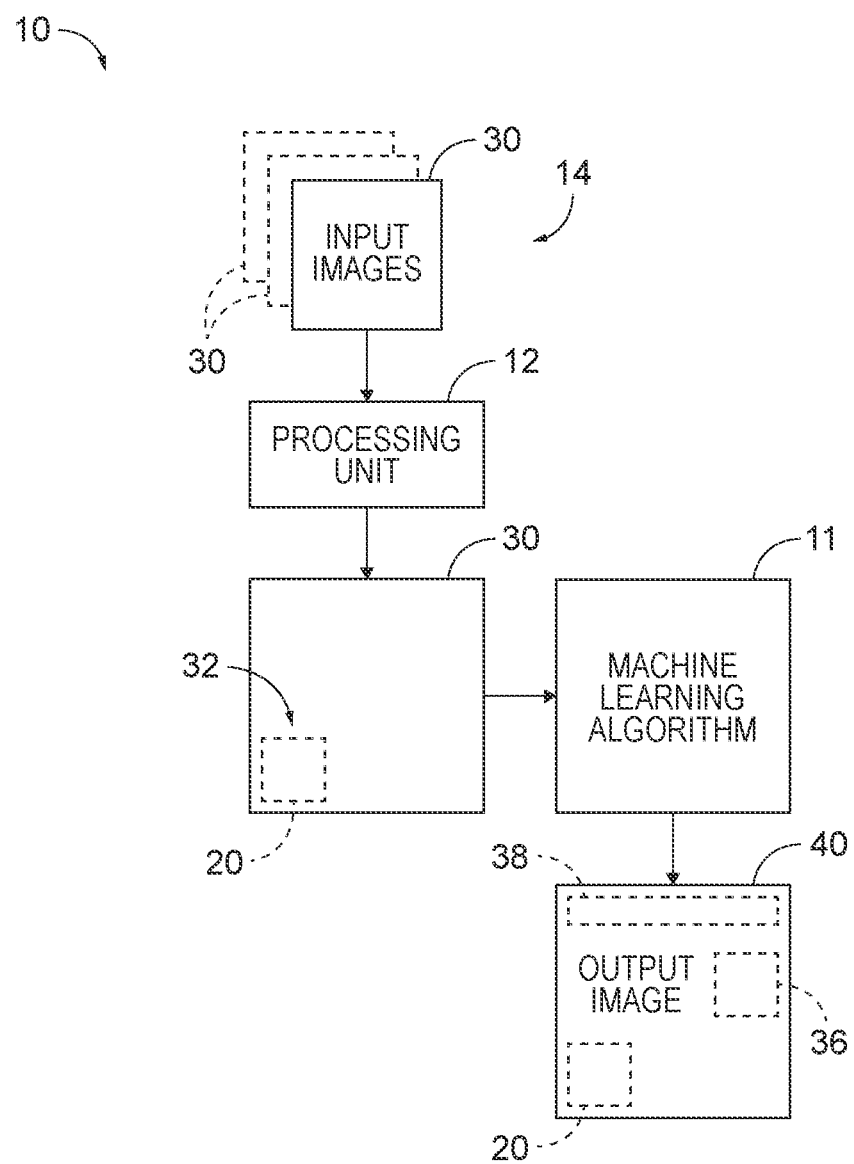
FIG. 2 is another schematic representation of non-exclusive examples of systems for detecting medical conditions, according to the present disclosure.

FIGS. 1-2 provide illustrative, non-exclusive examples of systems 10 according to the present disclosure. Elements that serve a similar, or at least substantially similar, purpose are labeled with like numbers in each of FIGS. 1-2, and these elements may not be discussed in detail herein with reference to each of FIGS. 1-2. Similarly, all elements may not be labeled in each of FIGS. 1-2, but reference numerals associated therewith may be utilized herein for consistency. Elements, components, and/or features that are discussed herein with reference to one or more of FIGS. 1-2 may be included in and/or utilized with any of FIGS. 1-2 without departing from the scope of the present disclosure.

In general, elements that are likely to be included in a given (i.e., a particular) example are illustrated in solid lines, while elements that are optional to a given example are illustrated in dashed lines. However, elements that are shown in solid lines are not essential to all examples, and an element shown in solid lines may be omitted from a particular example without departing from the scope of the present disclosure.

FIG. 1 schematically illustrates nonexclusive examples of systems 10 according to the present disclosure, showing systems 10 at a high level, overall perspective. Systems 10 include at least one processing unit 12 which includes a machine learning algorithm 11. In some examples, machine learning algorithm 11 may be accessed by processing unit 12, rather than stored therein. Processing unit 12 is programmed to receive an image input 14 from an imaging device 16, with image input 14 being one or more images, slides, and/or videos that are obtained and/or produced by imaging device 16. For example, image input 14 may include digitized pathology slides, videos, CT images, or any other type of image produced by imaging device 16. Imaging device 16 may be, for example, a sonography device, an x-ray device, a computed tomography (CT) scanning device, a magnetic resonance imaging (MRI) device, a positron emission tomography (PET) device, a retinal camera, a dermatoscope, a radiograph device, a mammography device, an endoscope, a colonoscopy device, an esophagogastroduodenoscopy device, a bronchoscopy device, a photoacoustic endoscopy device, an electro-optical sensor, a Narrow Band Imaging (NBI) colonoscopy device, a white light endoscopy device, a chromoendoscopy device, and/or a capsule endoscopy device. Imaging device 16 may be located in the same facility as processing unit 12 in some examples. In other examples, imaging device 16 may be located in a different facility and/or location than processing unit 12. For example, one or more remotely located imaging devices 16 may send image input 14 to processing unit 12, such that machine learning algorithm 11 may be used to process and analyze data from a plurality of different imaging devices 16 concerning a plurality of different patients.

Processing unit 12 is further programmed to receive patient health data 18, which may also be known as metadata 18, as input. Patient health data 18 may be received from, for example, a computing device 28, which may store said patient health data 18 and/or be configured to access patient health data 18 from other sources such as manual input, electronic health records, electronic medical records, and/or other health/medical records or charts. Patient health data 18 may include patient health data that is entered in real-time (e.g., during or immediately before or after a procedure producing images via imaging device 16), patient health data from said medical records, dynamic state data (real-time, potentially continuously changing data), and/or static data regarding the patient. In some examples, patient health data 18 includes data that is collected or provided before image input 14 is provided to processing unit 12. For example, processing unit 12 may receive patient health data 18 that includes dynamic heart rate data synced with a colonoscopy procedure, along with patient's demographics accessed from medical records, along with information entered the day of the colonoscopy, such as information pertaining to the procedure indication, previous colonoscopy results and preparation quality, medications, and time since last food or drink consumed. As further illustrative examples, patient health data 18 may include survey question answers, static data, active data, electronic health records, electronic medical records, risk factors, body mass index (BMI), physical activity, cigarette smoking history, alcohol usage, family history, presence of inflammatory bowel disease, current hormone therapy (e.g., postmenopausal hormone therapy), former hormone therapy (e.g., postmenopausal hormone therapy), aspirin usage, nonsteroidal anti-inflammatory drugs (NSAIDs) usage, consumption of processed and/or red meat, fruit and vegetable consumption levels, demographic information, medications (e.g., aspirin, folate, multivitamins, prescription medications, etc.), drug usage, diet type and quality, dietary fat intake, weight, height, age, race, presence of other illnesses or diseases (e.g., Lynch syndrome, IBS, hereditary nonpolyposis, colorectal cancer, diabetes), biological markers (e.g., markers that may correlate with polyps or colon cancer or other medical condition being tested for, such as hemoglobin level, albumin, total protein, hemoglobin a1c, creatinine clearance, bilirubin, cholesterol profile, differential of white blood cells, c-reactive protein, and/or others), international normalized ratio (INR) test results, partial thromboplastin time (PTT) test results, prothrombin time (PT) test results, heart ejection fraction, platelet count, bleed time, previous endoscopy results, previous CT scan results, previous angiogram information, previous MRI results, previous PET results, computed risk predictors, blood work, prior procedural results, ASCVD risk, liver failure factors, autoimmune risk factors, Fong Clinical Risk Score for Colorectal Cancer Recurrence, and/or previous sonography (e.g., ultrasound) data. Results from previous tests or procedures can indicate previously-identified high-risk areas and/or areas that were poorly visualized, such that these areas can be given special attention during the current medical imaging procedure. Additionally or alternatively, patient health data pertaining to previous tests or procedures can indicate areas of increased signal intensity, such as in the case of prior CT scans, MRIs, and/or sonography. In some examples, results from previous tests or procedures can give location information about prior surgeries or treatments, such as the location of a previous polypectomy performed on that patient. In a specific example, patient health data 18 may include information regarding a patient's cardiac cycle and/or breathing cycle, with image input 14 being temporally annotated such that each of one or more images 30 from imaging device 16 may be matched with a phase of the patient's cardiac cycle and/or breathing cycle. Such temporal annotation (e.g., time stamps) may be relative (e.g., chronologically ordering each image 30 with respect to the other images 30 if image input 14) and/or absolute (e.g., mapped to the specific time of day that each image 30 was taken).

Systems 10 provide advantages over the prior art in how they can aggregate and combine temporally dissimilar data sources (e.g., real-time image data, real-time dynamic state information, and/or previously collected patient health data) to infer or determine a medical condition state determination in real-time. This may be accomplished both by integrating the data into a data tensor prior to input into machine learning algorithm 11, and/or optionally integrating the data into a data tensor for usage in machine learning algorithm 11. In some examples, previously collected patient health data 18 may be abstracted, or converted, into a numerical data representation (e.g., a data tensor or vector) that is conducive to combining with real-time sensor data and/or with image input 14 that has been converted to tensor data within machine learning algorithm 11. This may enable systems 10 to utilize a single data representation that can be acted upon by machine learning algorithm 11 by combining these multiple sources and types of data together. Disclosed machine learning algorithms 11 may exhibit improved accuracy and/or availability in medical condition state determinations, as compared to human diagnosis and/or prior art artificial intelligence diagnoses, due to the elimination of subjectivity and the introduction of objective decision-making processes based on training of machine learning algorithm 11. Prior art machine learning models are not equipped to incorporate such patient health data from different points in time and have less access to data, and thus are less capable of evaluating the patient as a whole.

To this end, processing unit 12 is programmed to encode patient health data 18 thereby to transform, or convert, patient health data 18 to encoded patient health data 20, and transmit encoded patient health data 20 into machine learning algorithm 11 (e.g., feed, transfer, digitally transfer, deliver, or transport encoded patient health data 20 to, or into, machine learning algorithm 11). Said encoded patient health data 20 may be in the form of a data vector or tensor, and/or in the form of coded image pixels, as will be described in more detail herein. Based on image input 14 and encoded patient health data 20, processing unit 12 is programmed to make a medical condition state determination via machine learning algorithm 11. In an illustrative, non-limiting example, image input 14 may be images and/or video footage from a colonoscopy procedure obtained from imaging device 16 in the form of a colonoscopy device. Machine learning algorithm 11 may be trained to analyze this image input 14, along with encoded patient health data 20, to make a medical condition state determination, such as analyzing whether any of the images from the colonoscopy device show cancerous polyps.

Machine learning algorithm 11 is a convolutional neural network in some examples, which may be a fully trained convolutional neural network or a transfer learning convolutional neural network. In some examples, machine learning algorithm 11 is a custom convolutional neural network, while in other examples, machine learning algorithm 11 may employ a standard or generic convolutional neural network. Machine learning algorithm 11 typically is between 1 and 100 convolutional layers deep, though additional convolutional layers may be used in various examples. The number of fully connected layers of machine learning algorithm 11 also may be varied, such as to optimize the configuration of machine learning algorithm 11 such that it is adapted for a particular task or application. Some specific examples of disclosed machine learning algorithms include a total of between 5 and 20 layers. Additionally or alternatively, machine learning algorithm may be, or include, a transformer, a long short-term memory (LSTM), a recurrent neural network (RNN), a support vector machine (SVM), a dense neural network, an auto-encoder, and/or a vision transformer.

As described in more detail in connection with FIGS. 9-15, machine learning algorithm 11 may be trained and/or deployed according to presently disclosed methods. In some examples, machine learning algorithm 11 may be trained using datasets with labels created by unsupervised labeling (which may also be referred to as auto-labeling), semi-supervised labeling, and/or supervised labeling, or manual labeling. In some examples, supervised labeling is performed before semi-supervised and/or unsupervised labeling. In some examples, supervised labeling and unsupervised labeling initially are performed to train machine learning algorithm 11, with semi-supervised labeling being performed as needed or desired to improve and/or refine labels in the dataset. As used herein, "supervised labeling" (or "manual labeling") refers to labels that are assigned to images by a human, "semi-supervised labeling" refers to a process where a human labels a plurality of images (often a few hundred images), training a rudimentary machine learning algorithm using these labeled images, and then letting the trained algorithm make a guess at the labels for the rest of the thousands of images, then the human verifies that all those automatically assigned labels by the algorithm are indeed correct, and "unsupervised labeling" refers to automated algorithms for labeling training images without human supervision.

In some systems 10, processing unit 12 is further configured to receive sensor data 22, such as sound input, a near-infrared (NIR) spectroscopy input, 2D vector data, 3D vector data, and/or 4D vector data. For example, sensor data 22 may include sound input from a health care practitioner dictating information about the procedure being performed, which may be input to processing unit 12 and/or machine learning algorithm 11. As used herein, health care practitioners may include any health care worker performing the steps indicated, such as physicians, nurses, technicians, operators, physician's assistants, and/or nurse practitioners, in various examples. In a specific example, sensor data 22 may include a dictation that the patient's colon is spasming, which may be added to other input data received by processing unit 12, such as to annotate image input 14 with temporal information (sensor data 22) observed by the health care practitioner. Additionally or alternatively, sensor data 22 may include a verbal instruction or command from the health care practitioner to alter something within system 10, such as to change a view or setting of imaging device 16. In a specific example, imaging device 16 may have two or more different recording modes, and sensor data 22 may include a sound input instruction to change from one type of recording to another, such as to change imaging device 16 from its standard recording mode to a near-infrared (NIR) mode, which may be used to better visualize a potential or suspected polyp or other medical condition state. In other examples, imaging device 16 may include capabilities for white light endoscopy, autofluorescence imaging (e.g., with magenta areas on the surface of potentially or suspected polyps), and/or magnifying endoscopy with narrow band imaging (e.g., to visualize a modified pit pattern of the mucosa with an increased number of capillaries), with the active mode being selected by sensor data 22 (e.g., verbal instructions), in some examples. Patient health data 18 and/or sensor data 22 (and/or dynamic state information 49 described herein) may be input into processing unit 12 as an input tensor 24. In other words, processing unit 12 may be configured to receive patient health data 18 and/or sensor data 22 as one or more input tensors 24.

As mentioned above, processing unit 12 may be programmed to perform an encoding conversion to encode patient health data 18 and thereby convert patient health data 18 to encoded patient health data 20. In one example, patient health data 18 is converted to encoded patient health data 20 via one-hot encoding. For example, processing unit 12 and/or machine learning algorithm 11 may include an encoding algorithm 26, which may also be referred to herein as an encoding system 26, that is configured to convert patient health data 18 into encoded patient health data 20. In some examples, encoding system 26 may encode patient health data 18 before it is received by processing unit 12. In some examples, encoding system 26 may be stored in one or more memories of processing unit 12. In a specific example, encoding system 26 may be configured to convert data concerning patient risk factors into a numerical representation based on a predefined data schema (e.g., a data tensor), thereby converting patient health data 18 to encoded patient health data 20. Encoding algorithm 26 performs one or more processes that can be repeatedly executed on a given piece of information in the same way each time it is performed, via a set of highly defined rules, to produce encoded patient health data 20.

In some systems 10, processing unit 12 is further programmed to image encode patient health data 18 in addition to (e.g., after) or instead of performing one-hot encoding conversion of patient health data 18. Additionally or alternatively, processing unit 12 and/or machine learning algorithm 11 may be programmed to perform a reshaping operation on at least one image of image input 14 to change the dimensionality of at least one image of image input 14 (e.g., transforming image input 14 to a single column vector or to a multi-dimensional tensor). For example, said reshaping operation may include a flattening operation to flatten image input 14 to a tensor representation. In some examples, encoded patient health data 20 may be concatenated onto the tensor representation of image input 14 (e.g., to the reshaped image input 14). Additionally or alternatively, processing unit 12 and/or machine learning algorithm 11 may be programmed to perform a concatenating operation to concatenate encoded dynamic state information 49 onto a tensor representation of least one image of image input 14. In other words, data from one or more sources (e.g., encoded patient health data 20 and/or encoded dynamic state information 49) may be concatenated onto reshaped image input 14 in some examples. As is understood in the art, flattening operations may be performed to reshape tensor data dimensions into a vector, which can then be appended to, or with, other data (e.g., other one-dimensional data) within machine learning algorithm 11. In some examples, the reshaping, flattening, and/or concatenating is performed prior to or within a fully connected network portion of machine learning algorithm 11 (which may also be referred to herein as a multi-layer perceptron portion of machine learning algorithm 11).

As noted, system 10 is configured to perform one or more medical condition state determinations, via machine learning algorithm 11, based on image input 14 and encoded patient health data 20. Such medical condition state determinations may be made continuously and/or in an automated fashion after machine learning algorithm 11 has been trained. Additionally or alternatively, such medical state determinations may be made in real-time, offering an improvement over existing prior art machine learning algorithms. Specifically, machine learning algorithm 11 may be configured to detect, classify, and/or localize one or more medical condition states based on the one or more images from imaging device 16 (e.g., image input 14), patient health data 18, encoded patient health data 20, and/or encoded dynamic state information 49. In other words, as used herein, "medical condition state determinations" include detecting, classifying, and/or localizing medical conditions shown in image input 14 (including determining a lack or absence of any medical conditions), via machine learning algorithm 11. For example, in the case of a colonoscopy procedure, machine learning algorithm 11 may detect a polyp in one or more images of image input 14. Additionally, machine learning algorithm 11 may classify the polyp detected in an image. Such classification may be a simple binary classification differentiating between the presence or absence of a polyp in a given image. In other examples, the classification may be more complex, selecting from among a plurality of classes of different types of polyps. Additionally or alternatively, machine learning algorithm 11 may localize the polyp, such as by pinpointing the location of region of image input 14 that contains the detected polyp, thereby determining the specific location or region of the polyp within image input 14. For example, machine learning algorithm 11 may be configured to define the image plane coordinates of the location of image input 14 in which a polyp was detected in the image frustum volume. In some examples, this information may be used to guide future management and/or recommendations pertaining to the detected medical condition state.

Such medical condition state determinations made by machine learning algorithm 11 are displayed for and/or communicated to a user of system 10, generally by converting image 30 of image input 14 to an output image 40, as schematically represented in FIG. 2. In some examples, encoding algorithm 26 of processing unit 12 produces output image 40, though in other examples, output image 40 may be produced directly by machine learning algorithm 11. Generally, displaying the medical condition state determination(s) also includes displaying one or more images 30 from image input 14, and/or displaying encoded patient health data 20 along with the medical condition state determination, to create output image 40. In other words, system 10 is configured to provide visual output for (e.g., visualization of) medical condition state determinations via a graphical user interface (e.g., a display device 42), with the visual output being augmented with patient health data 18 such that information may be presented and viewed all together as a single source (e.g., all together in output image 40).

This output image 40 can take many different forms, such as, for example, using one or more bounding boxes 36 on an image, text 38, one or more shaped outlines, one or more visual indications on a screen or monitor, video, and/or one or more auditory signals (e.g., systems 10 may be configured to beep or produce other sounds with increasing volume and/or frequency depending on the level of the perceived risk currently shown). For example, as schematically represented in FIG. 2, one or more bounding boxes 36 may be displayed surrounding one or more features or portions of image 30, which may highlight or indicate the portions of interest of image 30 identified by machine learning algorithm 11. For example, if machine learning algorithm 11 detects a polyp in image 30, it may display bounding box 36 around said polyp in output image 40. In some examples, such bounding boxes 36 may be displayed in cases where machine learning algorithm 11 has a threshold level of confidence with respect to the feature within image 30. In other words, processing unit 12 may be configured to determine a probabilistic diagnosis of the medical condition state of image input 14, based on image input 14 and encoded patient health data 20. Text 38 may include, for example, the medical condition state determination, a confidence level of the conclusion reached by machine learning algorithm 11, information as to localization and/or classification of the medical condition state, and/or other information about image 30 (e.g., patient information, time or date at which image 30 was taken, etc.). To this end, system 10 may include display device 42 (FIG. 1), such as a monitor or screen, that is configured to display, store, send, communicate, and/or print output image 40. In other words, output image 40 may include one or more printed output images and/or one or more digital output images. Machine learning algorithm 11 may interface with display device 42 and/or other hardware, communications systems, and/or apps to display and/or communicate information from the medical procedure and medical condition state determinations from machine learning algorithm 11. In some examples, display device 42 includes a head mounted display, an augmented reality device, a LCD (liquid crystal display) device, a LED (light emitting diode) device, and/or a plasma display device. Machine learning algorithm 11 also may be configured to output recommended treatments and/or products as a result of the medical condition state determination.

In some examples, system 10 may be configured to initially display data (e.g., encoded patient health data 20) to a user or practitioner in an enlarged or more readable fashion, and then later compress the size of the displayed data such that it is less obtrusive. For example, while machine learning algorithm 11 may be able to be informed by a single pixel of encoded patient health data 20, a human user may not be able to see a single pixel, and/or may have an easier time understanding or interpreting displayed data that includes labels, colored text, icons, diagram features, and/or larger areas of encoded data (e.g., collections of coded image pixels 34). In some examples, system 10 is configured to display real-time data or information during the medical imaging procedure. In some examples, system 10 includes an image display rendering function 41 (FIG. 1) which may be configured to render output image 40 to be displayed by display device 42. In some examples, image display rendering function 41 may be a component or feature of machine learning algorithm 11, and/or image display rendering function 41 may be a component or feature of processing unit 12. In other examples, image display rendering function 41 may be a component or feature of display device 42, or may be a standalone processing unit that creates output image 40 from the results of machine learning algorithm 11. Image display rendering function 41 may be configured to overlay, append, add, integrate, overwrite, and/or otherwise display encoded patient health data 20 and/or encoded dynamic state information 49 onto one or more images of image input 14, to be displayed and/or communicated by display device 42 as output image 40.

Specific examples of data that may be displayed to a user or practitioner during the medical procedure and/or in output image 40 may include polyp count (with presumed pathology displayed and appropriately modifying the previously established pretest probabilities), predicted distance into the colon, upcoming landmarks and displaying current landmarks (such as ileocecal valve, appendiceal orifice, spleen, liver, terminal ileum, etc.), information from previous colonoscopies about polypectomies (and method used), tattooed colons, previous surgical resections, diverticula locations (which may assist in reducing the probability that an outpouching is not a polyp but instead an inverted colonic diverticulum), recommendations on anesthesia, alerts regarding anesthesia (e.g., if the patient is awakening, machine learning algorithm 11 could display a suggestion for additional anesthesia, a higher concentration of anesthesia dosage, and/or further titration of anesthetic medications), alerts requiring assistance (e.g. if the patient begins to cough, lidocaine could be suggested by machine learning algorithm 11), information regarding when imaging device 16 is approaching areas that were not well visualized on a previous colonoscopy, predictions as to the current part of the colon imaging device 16 is located in (as location heavily influences polyp and colonic cancer probability rates), a live probability of finding a polyp, a live probability of pathology of the polyp, the last given medication(s), suggestions for new medications to be administered (e.g. propofol, lidocaine, etc.), information on renal/hepatic clearance, volume distribution, liver failure, and/or creatinine level. Additionally or alternatively, systems 10 may display data to the user or practitioner at the end of the medical imaging procedure, which may include information such as the predicted/recommended return year for a subsequent medical imaging procedure, information about the current medical imaging procedure to assist billing, documentation, and self-improvement (e.g., time and method spent removing polyps, time to cecal intubation, time withdrawing, etc.), a predicted model of the colon with areas poorly visualized on it to assist any subsequent colonoscopy to ensure complete observation of colon, a procedure duration and event timestamps based on visually identified patient anatomical features, and/or a summary of the colonoscopy procedure with relevant details and screen captures of polyps. Such information may, in some examples, be provided in a billable report that automatically generated for the patient by disclosed systems 10. Of course similar metrics and relevant data may be provided and displayed as described herein for medical imaging procedures other than colonoscopies as well.

Additionally or alternatively, systems 10 may be configured to produce a sound (e.g., an auditory signal) to communicate information about findings from machine learning algorithm 11, one or more medical condition state determinations, or etc. In some examples of system 10, processing unit 12 is programmed to cause display device 42 to emit such sounds, and/or processing unit 12 itself may be configured to produce the auditory signals, such as via a speaker or other auditory output device. For example, system 10 may be configured to produce a particular sound when a particular medical condition is detected, such as a beep or other sound when a polyp is detected, in real-time during the medical procedure. In some examples, the volume (e.g., magnitude and/or amplitude), frequency, and/or tone or type of sound may change depending on (e.g., proportionally to) the type of medical condition detected, the classification or seriousness of the medical condition detected, and/or the confidence of machine learning algorithm 11 in the determination. For example, the produced sound may be louder when machine learning algorithm 11 reports a higher confidence level in a medical condition state determination, and quieter when machine learning algorithm 11 reports a lower confidence level in the medical condition state determination. In some examples, the auditory signal may be a pre-recorded sound or synthesized voice announcement of a medical condition state determined by machine learning algorithm 11 and/or the associated confidence level of said medical condition state determination. Additionally or alternatively, the pre-recorded sound or synthesized voice may include information about the confidence level of machine learning algorithm 11 and/or recommended corrective action. In some examples, the pre-recorded sound or synthesized voice may include information warnings or alerts, such as maintenance actions recommended for the system. In an illustrative example, one auditory signal may provide information such as "polyp detected with 52% confidence, lighting is poor, clean camera," which can alert a user to a need for better preparing the system and/or environment for more accurate input information.

Additionally or alternatively, systems 10 may be configured to automatically generate an output report, or summary report, for the health care practitioner and/or for the patient. For example, systems 10 may be configured to generate this report at the end of procedure, which may provide the patient a summary (e.g., printed and/or in an electronic format) of the findings (e.g., the medical condition state determination), future appointments or procedures that are scheduled, and/or treatment recommendations. Additionally or alternatively, such output reports may include one or more output images 40 produced by systems 10. Additionally or alternatively, output reports generated by systems 10 may include billing information for the procedure. In some examples, systems 10 may be configured to ask or prompt the health care practitioner for a confirmation of the procedure (e.g., "An adenomatous polyp was piecemeal removed and initially 8×5 cm in the sigmoid colon; it was removed with hot biopsy forceps; is that correct?"), to which the practitioner may be able to respond verbally and/or via an input button or key. Systems 10 may be configured to ask or prompt follow-up questions, such as "Would you recommend the patient to be re-examined in 3 months?" Responses from the practitioner and/or the automatically generated output reports including the same may be recorded by systems 10 for storage in the patient's medical records (e.g., systems 10 may be configured to electronically transfer the output report to the patient's electronic health record), for output reports generated by systems 10, and/or for reporting to the patient's insurance company. In some examples, systems 10 may be configured to automatically assign a billing code (e.g., from a lookup table) for the procedure performed. In some examples, the output report generated by systems 10 may include images of the polyp (or other medical condition) before and after removal, expected distance from rectum or other anatomical features, and/or a map or image of the 3D expected polyp location within the patient's body. For example, the output report may mark or indicate the type of polyp found, what procedure was performed, and/or recommended follow-up (e.g., return in 3 months for a repeat or other monitoring). Output reports generated by systems 10 also may indicate areas where visualization was less than ideal. In some examples, systems 10 may be configured to generate different output reports for different parties, such as one output report for the patient with information relevant to the patient, and a different output report for the patient's insurance company, which may include information specifically needed by the insurance company but less useful to the patient.

Turning now to FIGS. 3-8, illustrative non-exclusive examples of output images 40 are illustrated. Where appropriate, the reference numerals from the schematic illustrations of FIGS. 1-2 are used to designate corresponding parts in FIGS. 3-8; however, the examples of FIGS. 3-8 are non-exclusive and do not limit output images 40 to the illustrated examples. That is, output images 40 are not limited to the specific examples illustrated in FIGS. 3-8, and may incorporate any number of the various aspects, configurations, characteristics, properties, etc. that are illustrated in and discussed with reference to the schematic representations of FIGS. 1-2 and/or the examples of FIGS. 3-8, as well as variations thereof, without requiring the inclusion of all such aspects, configurations, characteristics, properties, etc. For the purpose of brevity, each previously discussed component, part, portion, aspect, region, etc. or variants thereof may not be discussed, illustrated, and/or labeled again with respect to each of FIGS. 3-8; however, it is within the scope of the present disclosure that the previously discussed features, variants, etc. may be utilized therewith.

Figure 3:
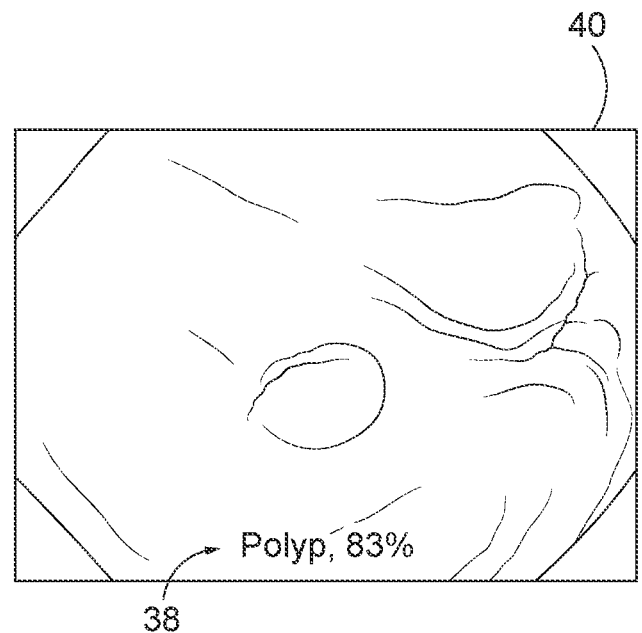
FIG. 3 is an example of an output image produced by presently disclosed systems.
Figure 4:
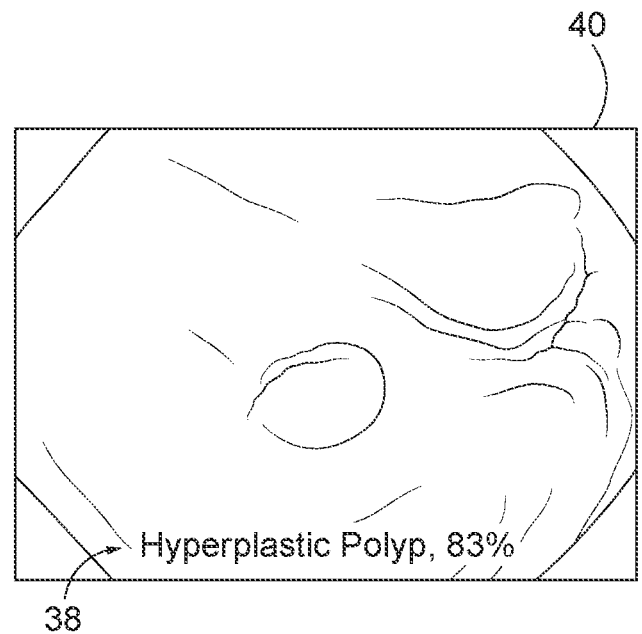
FIG. 4 is an example of an output image produced by presently disclosed systems.

FIGS. 3-6 show illustrative examples of output images 40 that may be produced by presently disclosed systems 10. In FIG. 3, output image 40 shows an image from a colonoscopy procedure (e.g., an image input from an imaging device according to one example of system 10), with text 38 indicating a medical condition state determination, along with the probabilistic determination of that medical condition state determination (e.g., the confidence of machine learning algorithm 11 in the medical condition state determination). In the example of FIG. 3, text 38 indicates that machine learning algorithm 11 determined that there is an 83% probability with a confidence interval that output image 40 includes a polyp, based on the training model. In the example of FIG. 4, output image 40 includes the same image from the colonoscopy procedure, and text 38 indicates an 83% probability that output image 40 shows a hyperplastic polyp, based on the training model. In other words, in the example of FIG. 4, output image 40 includes the image along with the expected pathology type shown. In this example, text 38 indicates a classification of the feature (e.g., the polyp) detected by machine learning algorithm 11.

Figure 5:
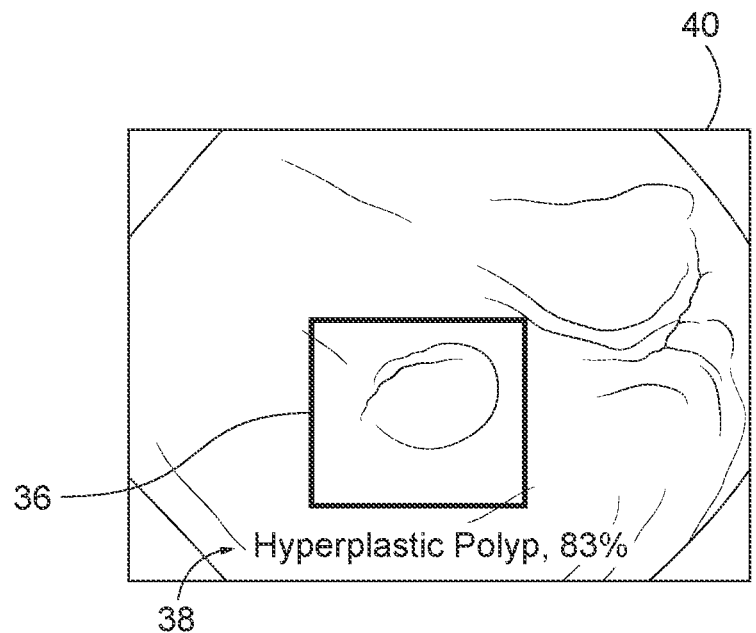
FIG. 5 is an example of an output image produced by presently disclosed systems.

In the example of FIG. 5, output image 40 includes the same text 38 as in FIG. 4 (with the classification and probability of the medical condition state determination), and also includes bounding box 36 that has been added to the image input such that bounding box surrounds, or is positioned around, the feature in question. While bounding box 36 is illustrated as rectangular in shape, bounding box 36 may be any desired shape, such as circular, polygonal, a line or combination of lines, an arrow, a shaped outline roughly matching the identified medical condition, and/or any other graphical indication as to the location of the detected medical condition on the image. Specifically, bounding box 36 is positioned on the image input to indicate the area within the image where machine learning algorithm 11 detected a polyp (or other feature, for other examples of system 10). Bounding box 36 may be displayed in a color that is optimized to highlight the presence of bounding box 36 (e.g., bounding box 36 may be displayed in a color that has a high contrast compared to the background image on which it is overlaid). Additionally or alternatively, bounding box 36 may be displayed in a particular color according to a coding scheme. For example, different colors of bounding boxes 36 may be used to indicate a different type or severity of medical condition state, and/or different colors of bounding boxes 36 may be used to indicate different confidence levels of machine learning algorithm 11. Additionally or alternatively, the actual feature of interest (i.e., a polyp) may have its appearance and/or color altered by machine learning algorithm 11 to highlight the feature in output image 40.

Figure 6:
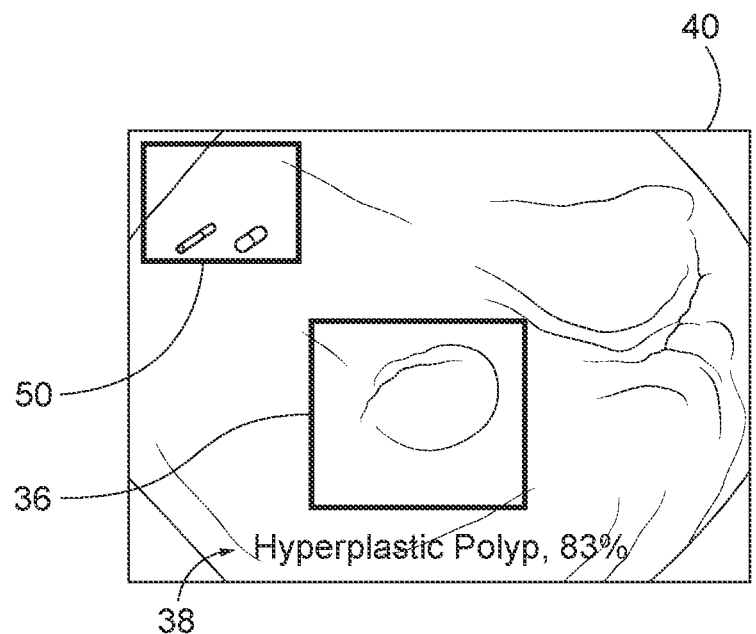
FIG. 6 is an example of an output image produced by presently disclosed systems.

In the example of FIG. 5, output image 40 includes the image input, pathology information, and bounding box 36, along with the medical condition state determination indicated by text 38. In the example of FIG. 6, output image 40 includes the same image input, text 38, and bounding box 36, and also includes risk factors 50, which may be represented in output image 40 using additional text and/or images or icons. Risk factors 50 may include those risk factors present in the given patient that inform the medical condition state determination made by machine learning algorithm 11. For example, if smoking is a known risk factor for a particular type of polyp and the image inputs being analyzed by machine learning algorithm 11 are from a patient who smokes, output image 40 may include an indication in risk factors 50 that the patient is a smoker. Additionally or alternatively, output image 40 may include semantic segmentation to focus machine learning algorithm 11 on a specific area of image input 14 and/or simplify image input 14 and/or output image 40.

Output image 40 may include additional or alternative information than is shown in FIGS. 3-6, such as current polyp count in real-time during the medical imaging procedure (or a current real-time count of another medical condition in types of procedures other than colonoscopies), predicted distance of travel of the imaging device within the patient's body, upcoming anatomical or physical landmarks or markers within the patient's body, information from previously performed medical procedures, recommendations on anesthesia, probability rates of cancer in a given area of the patient's body, a live probability of finding a polyp or other medical condition, a live probability of the pathology of a polyp or other detected medical condition, information on the most recent medication(s) the patient received, a predicated date for subsequent procedures, a predicted model of an organ of the patient being imaged, and/or summary information regarding the medical imaging procedure. Of course when the medical imaging procedure being evaluated is one other than a colonoscopy, such alternative information may be provided that specifically pertains to measurements, indications, and/or recommendations associated with that particular imaging procedure. For example, rather than polyp count, a machine learning algorithm 11 configured to evaluate images from an endoscopy of a patient's esophagus may display information about the number of tumors found during that endoscopy.

In some systems 10, processing unit 12 is configured to add encoded patient health data 20 to at least one image of image input 14, which may include appending encoded patient health data 20 to image training data (e.g., image input 14), overlaying encoded patient health data 20 onto the image training data, embedding encoded patient health data 20 into the image training data, and/or otherwise adding encoded patient health data 20 to the image training data such that machine learning algorithm 11 is informed and trained using both the image training data and encoded patient health data 20. In some examples, encoded patient health data 20 is embedded into at least one image of image input 14 at or before a time that machine learning algorithm 11 analyzes image input 14, such that machine learning algorithm 11 analyzes image input 14 together with encoded patient health data 20 embedded in the at least one image of image input 14.

Systems 10 may embed and display encoded patient health data 20 within a particular, predetermined region of at least one image of image input 14 for analysis by machine learning algorithm 11 and/or to display to one or more users of system 10. For example, as shown in FIG. 2, image input 14 may include a plurality of images 30, which may be taken from video footage, or may be photographs or other medical imaging output images. One or more images 30 may be converted by processing unit 12 such that encoded patient health data 20 is added to the one or more images 30. In the example of FIG. 2, encoded patient health data 20 is shown embedded in one of images 30 by processing unit 12, with encoded patient health data 20 being positioned within a region 32 of image 30.

In FIG. 2, region 32 is shown as being in the lower left hand corner of image 30, though in other examples, region 32 may be in any desired location with respect to image 30. In other various examples, region 32 may be located in the lower right corner, the upper right corner, the upper left corner, along the left side, along the right side, along the top, along the bottom, in a middle area, and/or within a perimeter of image 30. Region 32 generally is the same for each image 30 into which encoded patient health data 20 is embedded. For example, system 10 may be configured to display encoded patient health data 20 within the same region 32 each time images 30 are analyzed, so that users may easily find said encoded patient health data 20 within image 30. Some encoded patient health data 20 may be displayed for a temporary period of time during the procedure and/or analysis, and/or may be updated throughout the procedure. Some encoded patient health data 20 may be displayed for the duration of the procedure and/or analysis.

Machine learning algorithm 11 may be configured to process and interpret encoded patient health data 20 that is embedded in at least one image 30 in this manner. For example, encoded patient health data 20 may be encoded and embedded into image 30 as collections of coded image pixels 34 that are added to the image input (e.g., by image display rendering function 41). Collections of coded image pixels 34 may be any desired shape, size, and/or arrangement. In some examples, collections of coded image pixels 34 may include QR Codes®, microQR codes, IQR codes, QRGraphy, Frame QR, HCC2D, microQRJAB codes, JAB codes, ArUco codes, barcodes, one or more pixels configured to be detectable by machine learning algorithm 11, and/or one or more pixels arranged to be visible to a human eye. In other words, collections of coded image pixels 34 may employ any of various known data compression or encoding techniques.

Figure 7:
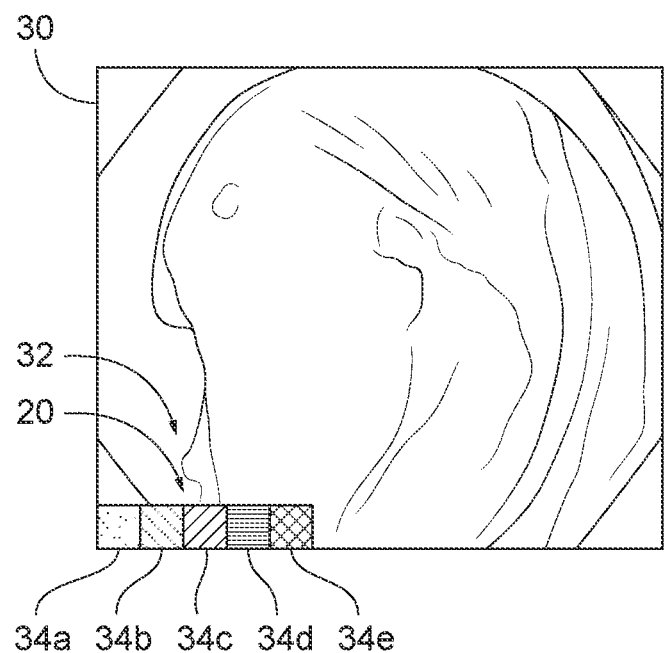
FIG. 7 is an example of an image produced by presently disclosed systems, with embedded encoded patient health data displayed on the image.

For example, FIG. 7 illustrates a specific example of encoded patient health data 20, shown as a plurality of collections of coded image pixels 34 (e.g., 34a, 34b, 34c, 34d, and 34e) added to region 32 of image 30. Again, said encoded patient health data 20 is added to image 30 by processing unit 12 of presently disclosed systems 10, such as by adding collections of coded image pixels 34 to image 30, though encoded patient health data 20 may be added to image 30 in other forms, in addition to or instead of said collections of coded image pixels 34. As the term is used herein, "adding" encoded patient health data 20 to image 30 includes appending collections of coded pixels 34 (or other forms of encoded patient health data 20) to image 30, and/or overlaying collections of coded image pixels 34 onto image 30. In other words, the term "adding" includes overwriting, appending, adding, padding, embedding, and/or other means of incorporating collections of coded image pixels 34 (or other representation of encoded patient health data 20) into image input 14. In some examples, collections of coded image pixels 34 may be overlaid onto image 30 by overwriting a portion of the pixels forming image 30, which may be performed when it is desired to retain the original dimensions of image 30. In other examples, collections of coded image pixels 34 may be appended to image 30, such as by being appended along one or more edges of image 30 (e.g., along the bottom of image 30), which may thereby change (e.g., increase) the overall dimensions of image 30. Encoded patient health data 20 (e.g., collections of coded image pixels 34) are generally displayed on output images 40 as well, after analysis by machine learning algorithm 11.

Collections of coded image pixels 34 may be configured such that they are discernible and understood by a human observer of system 10, as well as configured to by analyzed by and deliver information to machine learning algorithm 11. In some examples, said collections of coded image pixels 34 may encode patient health data 18 (FIG. 1) using a color-coded scheme. For example, each different type of patient health data 18 may be encoded using a different color, with different values being represented by the shade or darkness of that color (e.g., a respective shade of each respective collection of coded image pixels 34 may represent the relative value of the respective encoded piece of patient health data encoded in the respective collection of coded image pixels 34). In this manner, a plurality of collections of coded image pixels 34 may be generated such that a respective collection of coded image pixels 34 is displayed for each respective type or category of encoded patient health data 20.

As an illustrative example, collection of coded image pixels 34a may be a blue collection of pixels representing the patient's age, with the patient's age represented by the shade of blue shown (e.g., older ages may be shown in darker blue, while younger ages may be shown in a light blue). As other illustrative examples, collection of coded image pixels 34b may represent, or encode, the patient's gender using red pixels, collection of coded image pixels 34c may encode the patient's race using green pixels, collection of coded image pixels 34d may encode the patient's smoking habits using purple pixels, and collection of coded image pixels 34e may encode the patient's drug use using black pixels. Of course, these examples are only illustrative. Encoded patient health data 20 may be embedded into image 30 showing more or fewer different metrics or types of patient data, using textures or patterns, using different colors, and/or arranged differently than shown in this illustrative example. In some examples, collections of coded image pixels 34 may be encoded in gray-scale rather than color. In some examples, collections of coded image pixels 34 may be encoded using different colors for a single type of patient data (e.g., patient age may be represented by different colors of pixels for different age ranges, such as orange for one age range, and red for another age range). Collections of coded image pixels 34 also may be emphasized or highlighted in some examples, such as to flag for a practitioner a particularly relevant piece of patient health data.

Figure 8:
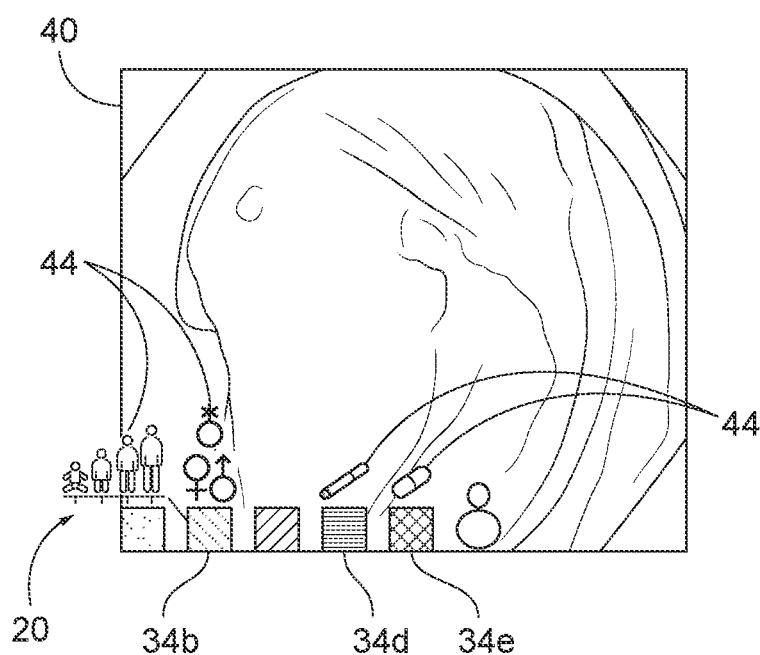
FIG. 8 is an example of an output image including visual output augmented by patient health data according to the present disclosure.

In some examples, such as shown in FIG. 8, an icon 44 may be displayed (e.g., in output image 40) to aid or facilitate visualization and interpretation of output image 40 by a human user (e.g., a physician or a technician using system 10). In other words, system 10 may be configured to display a respective icon 44 for each respective collection of coded image pixels 34 to indicate what the respective collection of coded image pixels 34 is encoding. For example, FIG. 8 shows a cigarette-shaped icon 44 positioned adjacent collection of coded image pixels 34d, which may be configured to encode the patient's smoking history. Said icons 44 may serve as a visual cue to human users as to what each collection of coded image pixels 34 represents or encodes, rather than requiring human users to remember what each respective color (or pattern, or texture, etc.) refers to. Additionally or alternatively, text labels may be displayed on output image 40 as a reminder of the meaning of collections of coded image pixels 34. Icons 44 and/or other types of labels may be produced by machine learning algorithm 11 and/or processing unit 12 (e.g., encoding algorithm 26 of processing unit 12), to be displayed in output images 40 produced by machine learning algorithm 11 after analyzing image input 14. Visualization aids such as icons 44 and/or labels may be displayed in real-time during the medical procedure, for real-time visualization and aggregation of information for the practitioner/user of systems 10.

Collections of coded image pixels 34 may be arranged in any suitable fashion when added to images 30. For example, collections of coded image pixels 34 may be arranged in a row, a column, and/or an array on one or more images 30. Generally, collections of coded image pixels 34 are positioned together, such that they are relatively close together, or adjacent each other. For example, collections of coded image pixels 34 may be positioned together such that they are all positioned within a given region 32 of image 30. In some examples, however, collections of coded image pixels 34 may be spread out or distributed in different regions 32 of image 30. For example, one or more collections of coded image pixels 34 may be located or displayed in one region 32, while one or more other collections of coded image pixels 34 may be located or displayed in a different region 32 of image 30.

Some systems 10 may include computing device 28 configured for collecting and/or retrieving patient health data 18, with computing device 28 being further configured to deliver patient health data 18 to processing unit 12. Additionally or alternatively, computing device 28 may be configured to collect and/or retrieve patient health data 18 in real-time from a database, such as from electronic health records and/or electronic medical records. In some systems 10, processing unit 12 itself may perform this function, while in other systems 10, processing unit 12 may access this information from computing device 28 or from another source. Patient health data 18 may include static data and/or processed information.

Some systems 10 may include an apparatus 46 for determining dynamic state information 48 of a patient, with said apparatus 46 also being referred to as a dynamic state apparatus 46. Dynamic state apparatus 46 may be configured to deliver dynamic state information 48 to processing unit 12. Dynamic state information 48 is information about the patient taken contemporaneously with a medical procedure that produces image input 14, which may be continuously changing in real-time. For example, dynamic state information 48 may be sensor-derived data obtained in real-time during a medical imaging procedure that produces image input 14. Dynamic state information 48 may be used to aid interpretation of images 30 obtained from imaging device 16 (e.g., dynamic state information 48 may provide information about the contents of images 30 that would not be obtainable by simply observing images 30 themselves. For example, increases in a patient's blood pressure may cause flaring of polyps present, which may change their appearance, such as making them appear larger than normal, and etc. Thus, when analyzing a given image 30 of image input 14, the patient's blood pressure (and/or other dynamic, real-time information at the time of the image) may be used in making medical condition state determinations with respect to that image. Similarly, if the patient's tissues are bleeding at all during the medical procedure, this can alter the appearance of polyps and other medical conditions within the patient, which machine learning algorithm 11 may be trained to identify and interpret. In other examples, dynamic state information 48 can dynamically affect the visual appearance of cancers or other medical conditions, and thus recording and storing this dynamic state information 48 may facilitate the medical condition state determinations made by machine learning algorithm 11.

Dynamic state information 48 may include, for example, the patient's heart rate during the procedure (i.e., real-time heart rate information), the patient's blood pressure during the procedure (i.e., real-time blood pressure information), compensated heart rate, anesthetics used during the procedure, telemetry, saline or other fluids used during the procedure, the patient's oxygen saturation during the procedure, end tidal carbon dioxide (capnography), the patient's current medications (e.g., those taken the day of the procedure), activity in distal extremities, positional data pertaining to imaging device 16 relative to the patient's body, positional data pertaining to sensors being used for measurements, temperature information (internal or external), and/or information regarding previous injuries or procedures performed on the patient such that image inputs 14 may be corresponded or mapped to areas within the patient's body that were previously injured, where applicable. Additionally or alternatively, dynamic state information 48 may include information regarding a patient's cardiac cycle and/or breathing cycle, such that image input 14 may be temporally annotated such that each of the one or more images 30 from imaging device 16 may be matched with a phase of the patient's cardiac cycle and/or breathing cycle. For example, with respect to the patient's cardiac cycle, one or more images from image input 14 each may be labeled as corresponding to diastole or systole, based on mapping respective time stamps from the respective image to time stamps from cardiac cycle data taken during the procedure. Additionally or alternatively, one or more images from image input 14 each may be labeled corresponding to P-wave, QRS complex, T-wave, and so on, of the patient's cardiac cycle. In various examples of system 10, dynamic state apparatus 46 may include one or more motion sensors, one or more accelerometers, and/or one or more video cameras configured for motion detection.

Similar to patient health data 18, dynamic state information 48 may be encoded by processing unit 12 to form encoded dynamic state information 49. Encoded dynamic state information 49 may be embedded into at least one image of image input 14, such as at or before a time that machine learning algorithm 11 analyzes image input 14. In this manner, machine learning algorithm 11 may be configured to analyze image input 14 together with dynamic state information 48 embedded in the at least one image of image input 14. Processing unit 12 is programmed to perform one-hot encoding conversion to encode dynamic state information 48, in some examples, such as via encoding system 26, which may also be referred to herein as an encoding algorithm 26. Processing unit 12 also may be configured to perform image encoding on dynamic state information 48, which may be performed after the one-hot encoding.

Machine learning algorithm 11 may be trained using manual, or supervised, labeling of image inputs 14 used during training. Additionally or alternatively, machine learning algorithm 11 may be trained using semi-supervised labeling information of image inputs 14 used during training. In some examples, the machine learning algorithm 11 may be configured to first receive supervised labeling, and then to receive semi-supervised labeling, and then to perform auto-labeling. In some examples, machine learning algorithm 11 is configured to first receive supervised labeling and/or to perform auto-labeling, and then to receive semi-supervised labeling to refine and improve labels in a dataset. In other words, system 10 may be configured to perform a labeling feedback loop that includes semi-supervised labeling, with such labeling feedback loop functioning to improve training efficiency of machine learning algorithm 11. In other words, manual labeling or semi-supervised labeling may be performed to assign a plurality of initial labels, followed by manual verification for at least a portion of the initial labels, to complete said labeling feedback loop.

This labeling feedback loop may enable machine learning algorithm 11 to be trained using "big data," which was not used for prior art machine learning models because they were not designed to continuously collect and aggregate large amounts of data. Prior art academic studies typically were designed to operate with a discrete and fixed size dataset. As opposed to prior art machine learning models, presently disclosed machine learning algorithms 11 may be configured to be continuously operating systems to automatically collect, aggregate, and organize data to streamline transmitting new data into machine learning algorithm 11. Thus, system 10 may be configured to receive big data for training machine learning algorithm 11, which can continuously improve performance of machine learning algorithm 11 as compared to prior art machine learning models, such as by improving accuracy and/or improve efficiency in learning patterns within the data. As used herein, big data currently includes datasets that are 1 terabyte or larger, though this definition is fluid and understandings may change over time as to what constitutes big data in the future. Additionally, because disclosed machine learning algorithms 11 are configured to automatically process, aggregate, and anonymize (e.g., de-identify) data (e.g., in an automated manner), this enables greater access to patient health data by making it easier or less onerous to comply with regulations protecting such data (e.g., because the automated nature of machine learning algorithms 11 may avoid the need for humans to directly access the protected data). In some examples, system 10 is configured for online learning such that machine learning algorithm 11 is updated using neural network weights, and thereby continues to learn as it receives additional image input 14 and patient health data 18 during use (e.g., after the initial training phase).

Thus, disclosed systems 10 may be configured to offer many advantages and features over prior art machine learning models. Presently disclosed systems 10 and machine learning algorithms 11 are repeatable, such that the overall machine learning algorithm 11 (including de-identification of patient health data and labeling processes) may be repeated any number of times for training and/or deployment of disclosed machine learning algorithms 11. The scale of data that may be used to train, and may be used as input to, presently disclosed machine learning algorithms 11 may be larger than possible with prior art machine learning models. Presently disclosed machine learning algorithms 11 may be configured to perform medical condition state determinations in an automated, continuous, and/or real-time fashion. Labeling feedback loops with semi-supervised labeling that are utilized by presently disclosed machine learning algorithms 11 can provide improved algorithm training efficiency and access to large scale data and/or big data, as compared to prior art machine learning models.

Furthermore, presently disclosed systems 10 encode patient health data (e.g., with one-hot encoding and/or reshaping operations) such that machine learning algorithms 11 make use of this meta-data in addition to image data, whereas prior art machine learning models make use only of image data. Thus, neural networks of the presently disclosed machine learning algorithms 11 are informed by both images from medical procedures and by encoded patient health data (generally originating as text data), which enables disclosed systems 10 to provide visual output showing the medical condition state determination that is augmented with consideration to patient history and other relevant patient health data, which is another improvement over prior art machine learning models. Thereby, systems 10 advantageously may be configured to inform physicians or other practitioners of patient history from a single source (e.g., output image 40), which may help enable the physician to identify patterns that are harder to observe when the data sources are separated, such as is the case in prior art imaging systems. Similarly, machine learning algorithm 11 may be able to observe patterns between patient history information and the medical procedure images that were not previously considered by prior art models or understandings, by the ability provided by systems 10 for machine learning algorithm 11 to simultaneously consider patient history along with the images from the medical procedure. These features may enable disclosed systems 10 to produce improved accuracy in its medical condition state determinations.

While FIGS. 1-8 give a high level representation of presently disclosed systems 10, FIGS. 9-15 schematically provide flowcharts that represent illustrative, non-exclusive examples of methods according to the present disclosure. In FIGS. 9-15, some steps are illustrated in dashed boxes indicating that such steps may be optional or may correspond to an optional version of a method according to the present disclosure. That said, not all methods according to the present disclosure are required to include the steps illustrated in solid boxes. The methods and steps illustrated in FIGS. 9-15 are not limiting and other methods and steps are within the scope of the present disclosure, including methods having greater than or fewer than the number of steps illustrated, as understood from the discussions herein.

Figure 9:
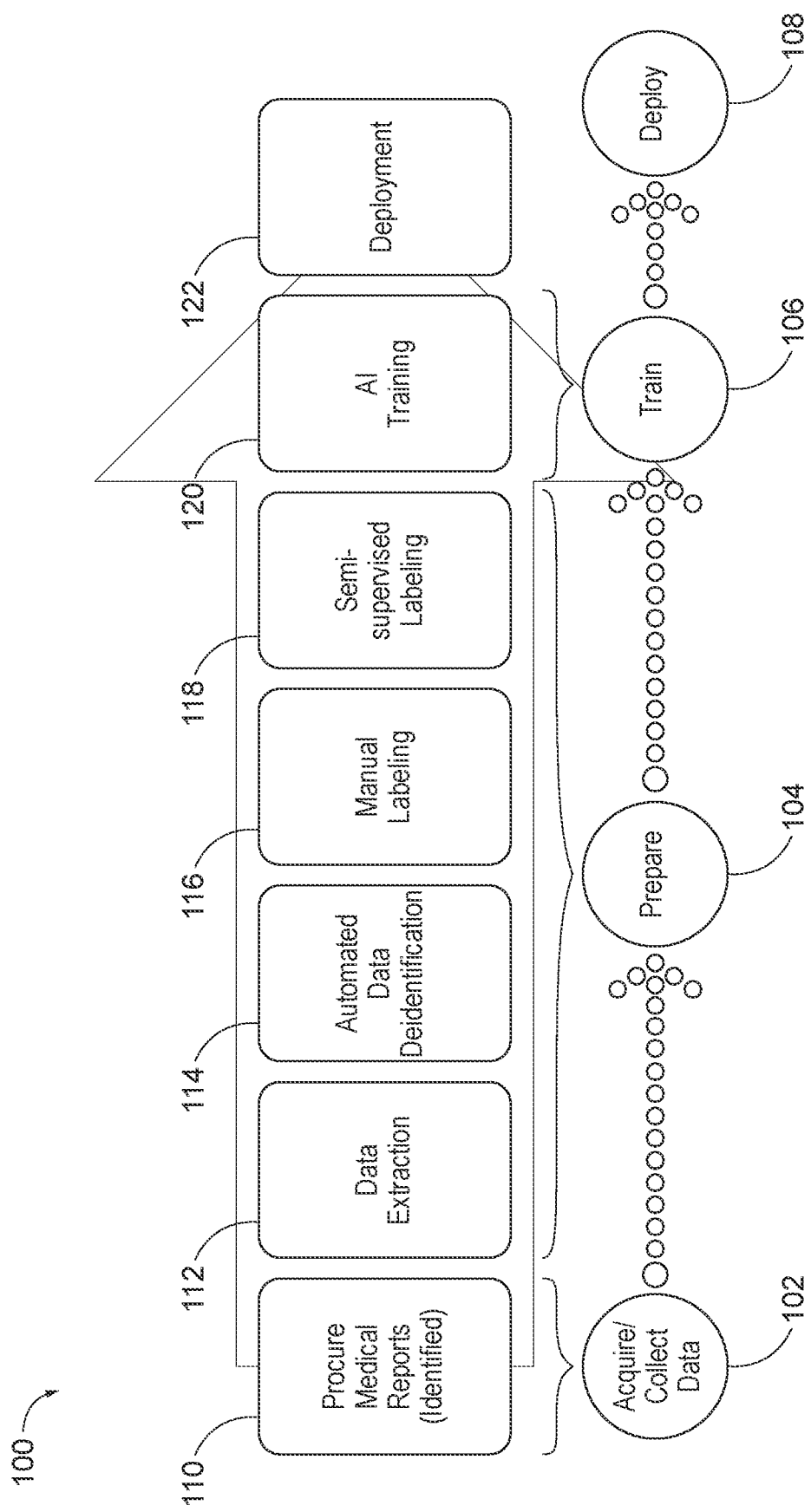
FIG. 9 is a high-level schematic flowchart of methods of preparing and training machine learning algorithms according to the present disclosure.

FIG. 9 gives a high level flowchart representation of related methods 100 associated with said systems 10. Overall, methods 100 generally include acquiring or collecting data to train machine learning algorithm 11, at 102, preparing the data for training machine learning algorithm 11, at 104, training machine learning algorithm 11, at 106, and deploying machine learning algorithm 11, at 108. In some examples, different method steps may be performed by different parties. For example, researchers or developers may primarily perform data collection at 102, data preparation at 104, and training at 106, while practitioners or other researchers may perform deployment at 108. FIG. 9 also illustrates additional aspects of each of these overall steps, each of which will be described in further detail herein.

Acquiring and/or collecting data at 102 may include, for example, procuring medical reports or datasets at 110. Additionally or alternatively, acquiring and/or collecting data at 102 may include collecting or acquiring data from electronic health records, electronic medical records, other health/medical records or charts, and/or from the patient directly, and may include acquiring and/or collecting data from multiple sources of any of the types of patient health data 18 discussed above. Preparing the data at 104 may include data extraction at 112 and/or data de-identification at 114. For example, data extraction at 112 may include extracting images from the data (e.g., medical reports) acquired at 110, and extracting text from the acquired data. In some examples, data extraction at 112 includes converting data extracted from the acquired data into a CSV file for later use by machine learning algorithm 11. Acquired datasets often include patient-identifying information, and this information may be removed during data de-identification at 114. Generally, de-identification of the data at 114 includes eliminating any identification of the patient associated with the meta-data (e.g., patient health data 18) in a database. The database may be a text-based database, though other database formats also may be used. For example, said database may contain the data sources in various forms: text, numerical, date, data array, and/or etc. In some examples, the data de-identification is automated. In other words, a computer system (e.g., processing unit 12, machine learning algorithm 11, and/or another computing system) may automatically de-identify the acquired data, at 114. In various examples, data de-identification at 114 may include assigning a universally unique identifier (UUID) to each individual represented in the acquired dataset(s), elimination of features from the acquired dataset(s), computing the patient's age, generation of a master database containing the original acquired dataset(s), and/or generation of a de-identified database containing the de-identified information to be used in training machine learning algorithm 11.

Once the datasets are acquired at 102, the data may be further prepared at 104, via manual labeling at 116 and/or semi-supervised labeling at 118, and then used to train machine learning algorithm 11 at 106, such as via artificial intelligence training at 120. In some examples, preparing the data at 102 to train machine learning algorithm 11 at 106 includes both manual labeling at 116 (which also may be referred to as supervised learning) and semi-supervised labeling at 118, with semi-supervised labeling at 118 being performed after manual labeling at 116. In some examples, preparing the data at 104 may include auto-labeling of the biological images, performed by machine learning algorithm 11.

Artificial intelligence training at 106, 120 may be phased, with training increasing in complexity as performance of machine learning algorithm 11 improves during training. For example, artificial intelligence training at 120 may include at least one phase, at least two phases, at least three phases, at least four phases, at least five phases, and/or six or more different phases. In a specific example, a first phase of artificial intelligence training at 120 may include evaluating model effectiveness based on visual interpretations of each respective biological image from the current model, a second phase may include measuring prediction accuracy based on respective pathology results for the respective biological specimen shown in the respective in situ biological image, a third phase may include updating the model weights based on the measured prediction accuracy of the respective pathology results for the respective biological specimen shown in the respective in situ biological image, in combination with bounding boxes 36 to identify an area of interest within the respective in situ biological image, and a fourth phase may include measuring accuracy based on respective pathology results for the respective biological specimen shown in the respective in situ biological image, in combination with bounding boxes 36 to identify an area of interest within the respective in situ biological image, and further based on the patient health data for the respective patient. Said phases of artificial intelligence training at 120 may be implemented serially or in parallel to train machine learning algorithm 11. In some examples, a respective dataset may be obtained for each respective phase of the plurality of training phases at 120, such that methods 100 may utilize a different respective dataset for each respective phase of the plurality of training phases at 120.

Once machine learning algorithm 11 is trained at 106, deployment at 108 may be performed. In other words, training machine learning algorithm 11 at 106 to classify, detect, and/or localize one or more medical condition states can enable said machine learning algorithm 11 to be deployed at 108 to classify, detect, and/or localize one or more medical condition states in new biological images obtained from new patients (e.g., biological images from patients that were not used in training machine learning algorithm 11).

Figure 10:
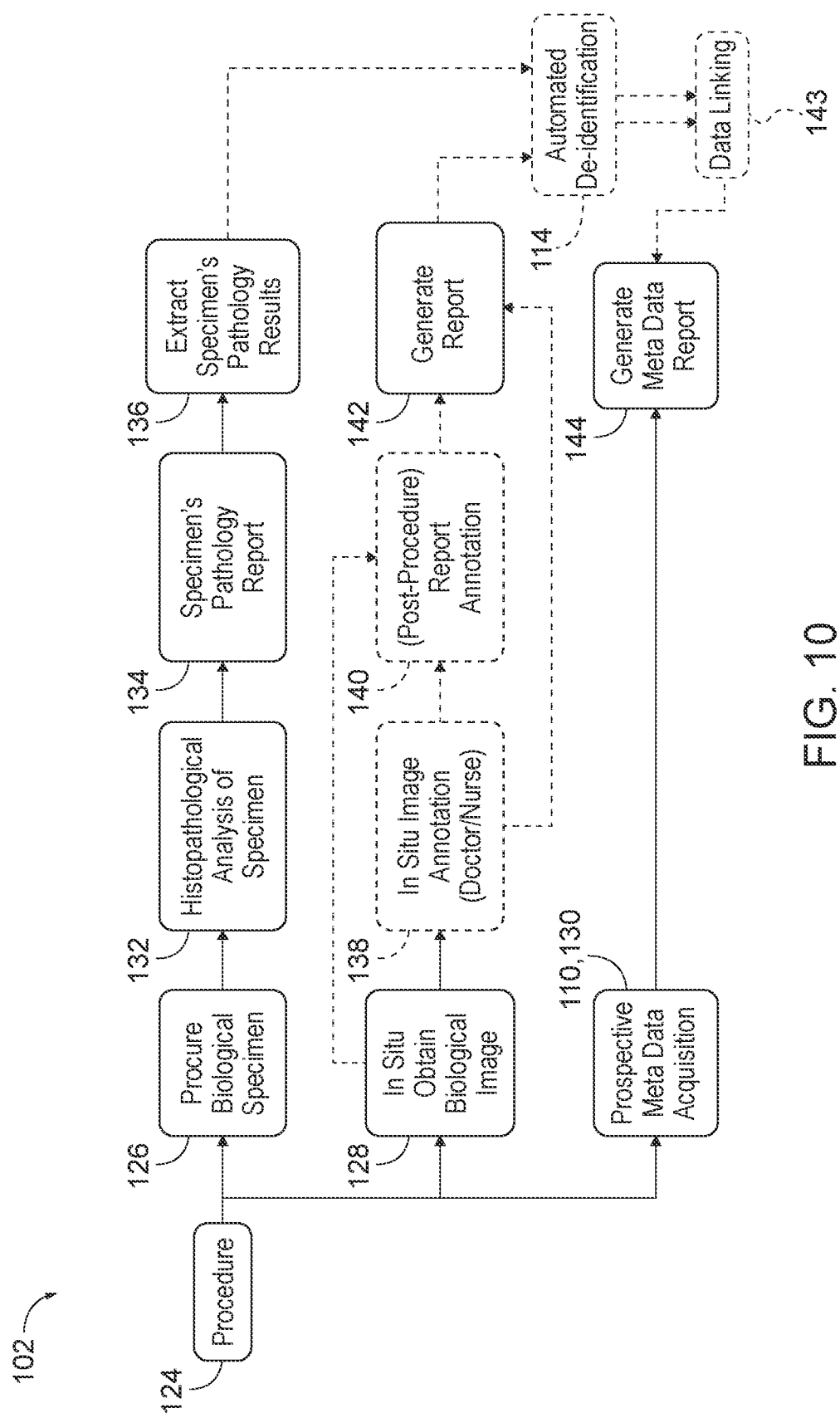
FIG. 10 is a schematic flowchart representation of methods of acquiring and/or collecting data for training disclosed machine learning algorithms.

FIGS. 10-15 break down individual steps of methods 100 from FIG. 9 into further details. FIG. 10 illustrates a more detailed view of acquiring or collecting data, at 102. Acquiring or collecting data at 102 generally begins by performing a medical procedure at 124. Said medical procedure may be prospective or retrospective in various examples. Performing the medical procedure at 124 may include performing any medical procedure that produces biological images and/or biological specimens. For example, performing the medical procedure at 124 may include performing a sonography procedure, an x-ray, a CT scan, an MRI, a PET scan, retinal imaging, dermatoscopy, radiography, a mammogram, endoscopy (e.g., lower endoscopy or upper endoscopy), a colonoscopy, an esophagogastroduodenoscopy, a bronchoscopy, photoacoustic endoscopy, a procedure using an electro-optical sensor, NBI colonoscopy, white light endoscopy, chromoendoscopy, and/or a procedure using a capsule endoscopy device. Additionally or alternatively, performing the medical procedure at 124 may include performing surgery, an excision, and/or a biopsy. Additionally or alternatively, performing the medical procedure at 124 may include examining the patient's external body, cancer detection, assessment of auto-immune diseases, assessment of drug-induced injuries, assessment of trauma-induced injuries, and/or infection assessment. Performing the medical procedure at 124 results in, or enables, procurement of one or more biological specimens at 126, obtaining one or more in situ biological images at 128, and/or acquisition of prospective patient health data at 130, which is a subset of procuring the medical reports at 110 of FIG. 9. Acquisition of prospective patient health data at 130 may include obtaining a plurality of medical reports for training machine learning algorithm 11, which may be obtained from, for example, electronic health records and/or electronic medical records.

In examples where acquiring or collecting the dataset at 102 includes procuring biological specimens at 126, said specimens may undergo histopathological analysis at 132, which may be used to generate a pathology report at 134. In other words, acquiring or collecting data at 102 may incorporate acquiring pathology results for the one or more biological specimens procured at 126. The specimen's pathology results may then be extracted, at 136, for inclusion in the dataset. In situ biological images of the specimen may be obtained at 128 in parallel with procurement of the biological specimen at 126, instead of procurement of biological specimens at 126, or before or after procurement of biological specimens at 126. In some examples, each biological image of the at least one in situ biological image obtained at 128 is at least 578×462 pixels, at least 1280×720 pixels, and/or at least 720×486 pixels in size. Prior art training methods used to train prior art machine learning models often could not or did not use these larger images as input, whereas disclosed machine learning algorithms 11 may be configured to accept such sizes of images as input. For example, publicly available models for polyp detection use lower resolution images as input, such as YOLO v3, which uses an image input of 416×416 pixels, and resnet152, which uses an image input of 224×224 pixels. Not using larger images as input limits the accuracy of some prior art machine learning models in interpreting the images and thus in making medical condition state determinations.

Said biological images may be annotated by a health care practitioner, such as a physician, a nurse, nurse practitioner, physician's assistant, or a technician, at 138. For example, a physician may annotate a biological image at 138 by indicating what is shown in the image, classifying a medical condition shown in the image, indicating where in the biological image a medical condition is visible, and/or measuring and indicating a size or dimensions of a medical condition in the biological image. As another example, annotation at 138 may include annotation by the patient themselves, such as in cases where machine learning algorithm 11 and/or processing unit 12 may interact with the patient to enter demographic or other information. Additionally or alternatively, a post-procedure report may be annotated at 140, and a report (e.g., a Provation® report) may be generated with respect to the biological image, at 142. Also, a patient health data report may be generated at 144 with the patient health data acquired at 130. Thus, the combination of the pathology results extracted at 136, the report generated about the biological images at 142, and the patient health data report generated at 144 for a plurality of patients and their respective procedures/biological specimens may together form a dataset that may be used to train machine learning algorithm 11. In some examples, de-identification may be performed at 114 on the pathology results extracted at 136 and/or on the report generated about the biological images at 142, and/or said data may be linked at 143, prior to generating the patient health data report at 144.

Figure 11:
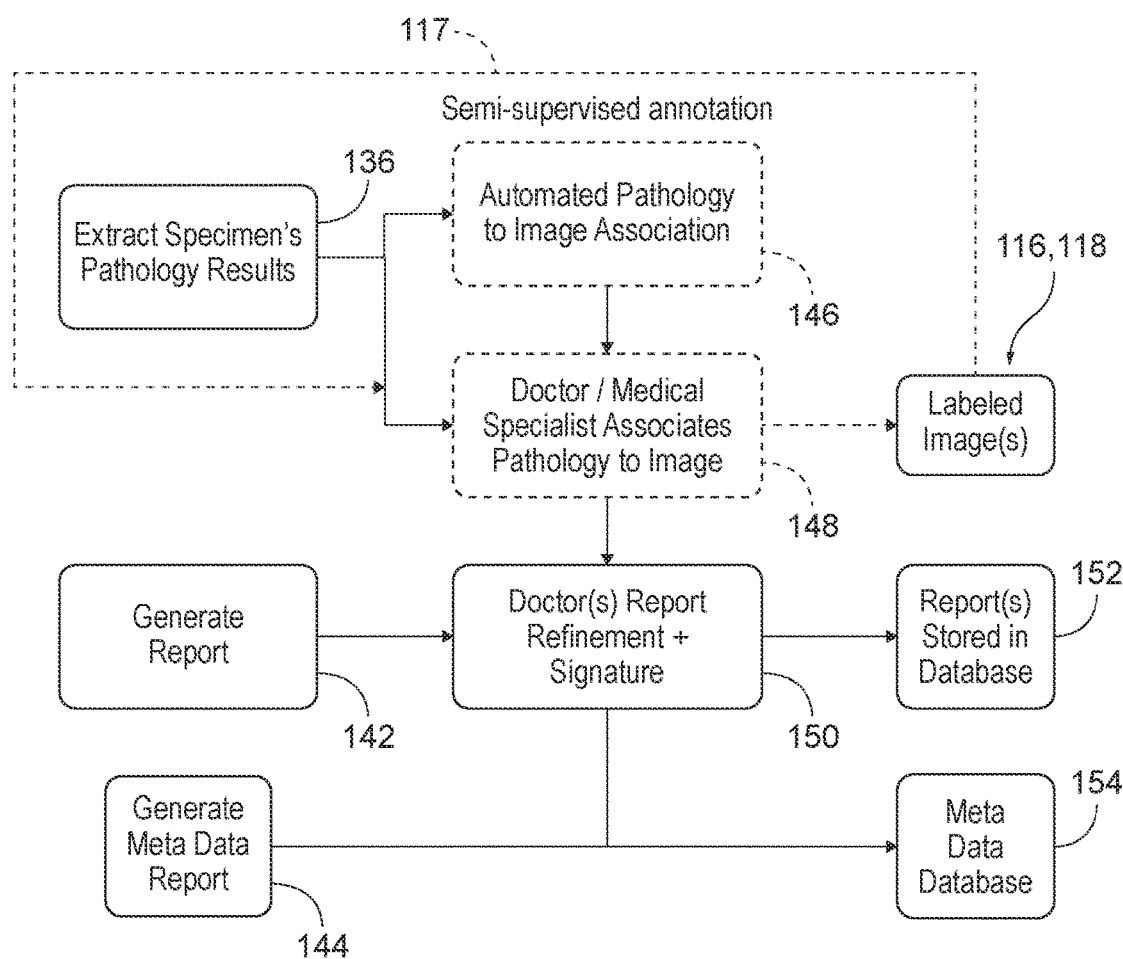
FIG. 11 is a schematic flowchart representation of methods of labeling data for training and preparing disclosed machine learning algorithms.

Said dataset acquired and/or collected at 102 may be manually labeled at 116 and/or subject to semi-supervised labeling at 118. With reference to FIG. 11, the specimen pathology results extracted at 136 may be used to create an association between the images and the pathology results at 146. Such association may be created automatically at 146, such as by machine learning algorithm 11. Additionally or alternatively, a practitioner may create associations between the images and the pathology results at 148. These associations created at 146 and/or 148 may be used to label the images from the medical procedure, at 116, 118. Similarly, the report generated from the in situ biological images at 142 may be refined and finalized by a practitioner at 150, and stored in a database at 152. The patient health data report generated at 144 may be stored in a patient health data database, at 154.

In some examples, labeling the images at 116 and/or 118 may include performing a labeling feedback loop, indicated at 117. Said labeling feedback loop may be performed by the processing unit and/or by the machine learning algorithm, and may involve performing manual and/or semi-supervised labeling on images that have already been labeled. Performing the labeling feedback loop at 117 may improve training efficiency of the machine learning algorithm, and/or enable training of the machine learning algorithm using big data.

Figure 12:
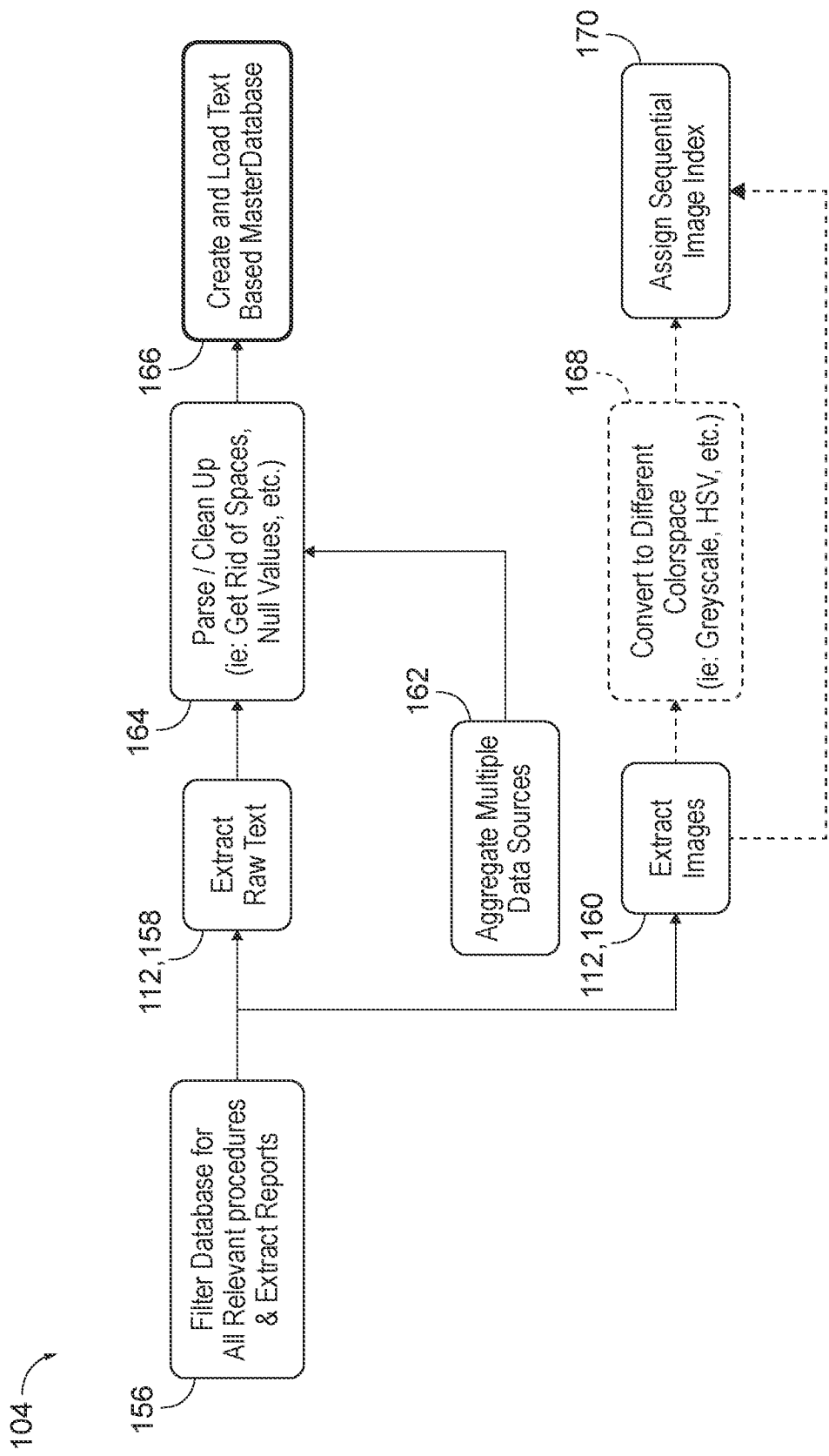
FIG. 12 is a schematic flowchart representation of methods of aggregating and preparing data for training disclosed machine learning algorithms.

With reference to FIG. 12, further details of preparing data for training machine learning algorithm 11 at 104 are described. The database where the reports about the in situ biological images are stored at 152 (FIG. 11) may be filtered and extracted at 156. For example, the database may be filtered for all relevant procedures, based on relevant features, for training machine learning algorithm 11. For example, the database may be filtered based on demographic information, weight, body mass index, habits such as alcohol consumption, smoking, and drug use, diet (e.g., read meat, fruit, and vegetable consumption), medications (e.g., nonsteroidal anti-inflammatory drugs, aspirin use, steroids, immunosuppressants, serotonin reuptake inhibitors, chemotherapy, etc.), familial medical history (e.g., history of colon cancer, acid reflux, lynch syndrome, heart disease, adenomatous polyposis, breast cancer genes), medical history (e.g., depression, heartburn, dyslipidemia), laboratory abnormalities (e.g., hemoglobin, BUN, LDL, troponin, MCV, differentiation of white blood cells), surgical history (e.g., cholecystectomy, polypectomy, colectomy, Nissan fundoplication, bariatric surgery), time of procedure, time since last procedure, bowel preparation, blood work results (e.g., red blood cell shape/count/distribution may be informative with respect to bleeding and/or cancer risk), and/or data from an endoscopy or other procedure (e.g., diagnosis code, phrasing, polyp description, time of day, etc.). Raw text may be extracted from a report generated by such filtering (step 156), at 158, and images may be extracted from the report at 160. Such text data extraction at 158 and image extraction at 160 are components of the data extraction step 112 of FIG. 9, and thus extracting text data at 158 and extracting images at 160 involve extracting text data and images from medical reports acquired at 110 (FIG. 9) and/or at 130 (FIG. 10).

Data may be aggregated from multiple sources and/or times, at 162, such as from the patient health data database generated at 154 (FIG. 11). For example, data may be aggregated at 162 that includes both real-time data and historical or previously collected data pertaining to the patient. Such aggregated data may be combined with the raw text extracted at 158, and then parsed and cleaned up, at 164. A master database may be created and loaded at 166, containing text data. As used herein "text data" may include text, numerical data, dates, times, etc. In parallel, the images extracted at 160 may be converted to different color spaces at 168, in some examples. For example, color images may be converted to greyscale, HSV, and etc. Finally, each in situ biological image may be indexed and assigned a sequential image index at 170. Said sequential image index typically will be based chronologically, though other indexes may be used in other examples. Image data from the indexing at 170 may be labeled at 116, 118 (FIGS. 9 and 11).

Figure 13:
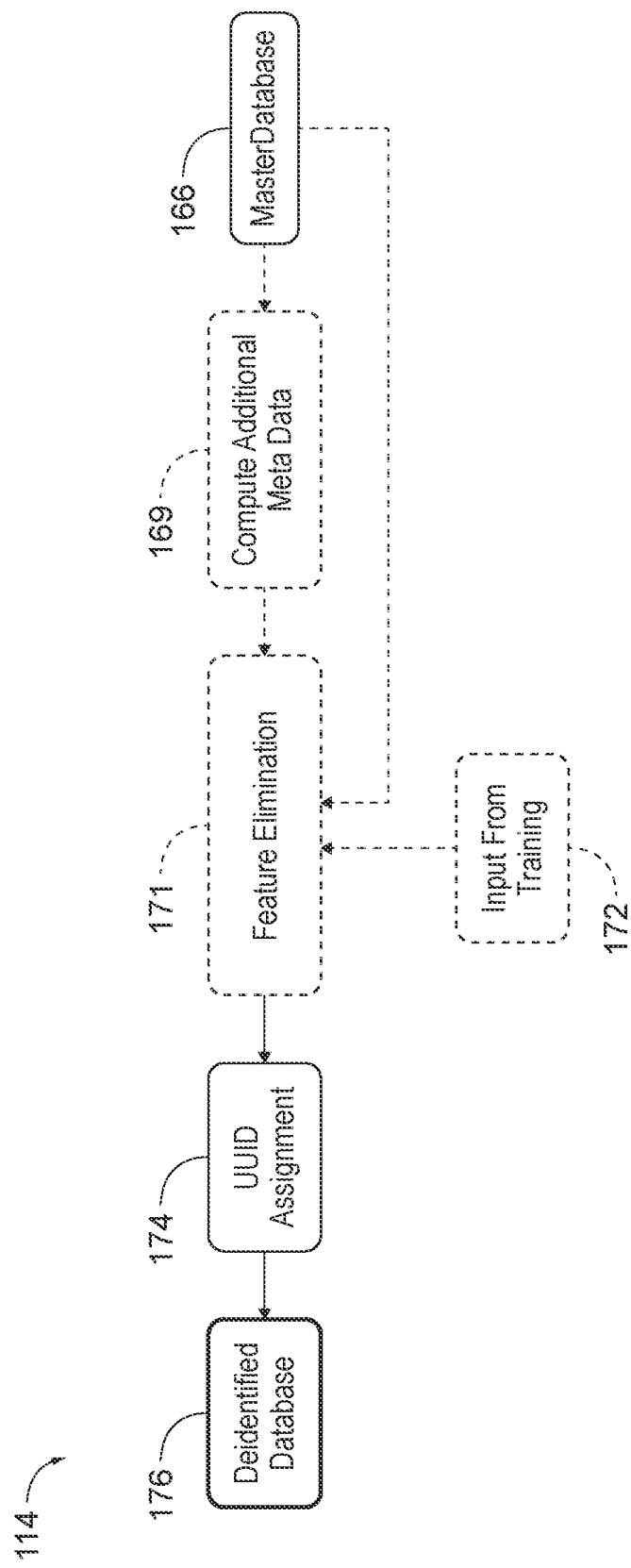
FIG. 13 is a schematic flowchart representation of methods of de-identifying and preparing data for training disclosed machine learning algorithms.

FIG. 13 provides some details regarding data de-identification at 114 (FIG. 9). The master database of text data created at 166 (FIG. 12) may be subjected to de-identification before being used to train machine learning algorithm 11. In some examples, additional patient health data may be computed at 169. For example, the patient's age may be computed rather than relying on an entered age for the patient in case mistakes are present. Methods 100 also may include feature elimination, at 171, in which unnecessary features or information are removed from the master database, according to the particular application of machine learning algorithm 11. In some examples, the feature elimination at 171 is performed manually, such that a practitioner or operator of the machine learning algorithm selects which features to remove from the master database at 171. Additionally or alternatively, input such as feature sensitivity analysis may be received from training the machine learning algorithm at 172 to inform which features should be eliminated at 171. In other words, feature elimination at 171 may be an automated elimination of features determined to be unnecessary by machine learning algorithm 11. The feature elimination at 171 may enable machine learning algorithm 11 to require fewer computing resources and/or increase processing speed. Additionally or alternatively, identification of salient parameters, features, and/or thresholds that are more important to decision-making in making medical condition state determinations (e.g., the feature elimination at 171) can improve processing speed and/or reduce network latency of machine learning algorithm 11. A UUID may be assigned to each individual or patient represented in the dataset, at 174, and thus a de-identified master database of data (e.g., text data) is completed at 176.

Methods of preparing and aggregating data at 104 and de-identifying data at 114 shown in FIGS. 12-13 may be automated, such that they are automatically performed by processing unit 12 and/or machine learning algorithm 11, via software programmed therein. For example, processing unit 12 and/or machine learning algorithm 11 may be programmed to automatically extract historically collected procedural images and text fields from PDF files (e.g., at 112, 158, 160 in FIG. 12), link this data with other historical patient health records (e.g., step 162 in FIG. 12), such as from the associated pathology reports, aggregate all the data into a single database (e.g., at 166 in FIG. 12) such as via a medical record identifier, de-identify personally identifiable data features (e.g., at 174 in FIG. 13), generate a complete de-identified database and identified database with linked image artifacts (e.g., at 176 in FIG. 13), keeping the de-identified database and linked artifacts physically separated to enable protection of patient privacy, and then use the de-identified data to train presently disclosed machine learning algorithms 11. Deidentifying the data at 114 may enable HIPAA data to be transformed into a protected format that can be accessed by individuals to support for supervised and semi-supervised labeling, while protecting patient confidentiality.

Figure 14:
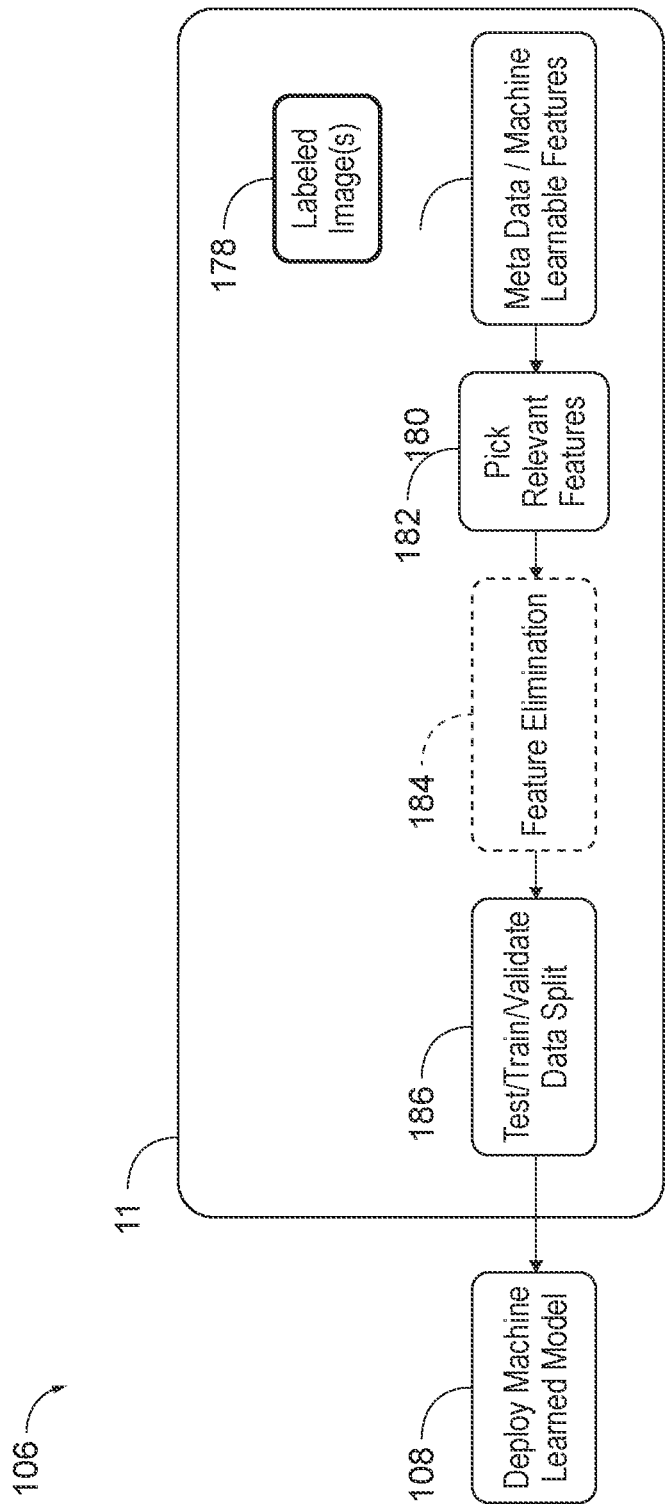
FIG. 14 is a schematic flowchart representation of methods of training and deploying presently disclosed machine learning algorithms for making medical condition state determinations.

With reference to FIG. 14, the image data that was indexed at 170 (FIG. 12) and/or labeled at 116, 118 (FIGS. 9 and 11) is input to machine learning algorithm 11, at 178, along with the text data from the de-identified database (at 176 in FIG. 13), at 180. Thus, methods 106 of training machine learning algorithm 11 use both image data and corresponding text data to train machine learning algorithm 11 to make medical condition state determinations, using the text-based database and the at least one labeled biological image. Thus, training machine learning algorithms 11 at 106 ultimately includes acquiring data from at least one medical procedure (e.g., performing the procedure at 124 in FIG. 10), including acquiring at least one in situ biological image of an area of a patient's body (at 128 in FIG. 10) and acquiring one or more biological specimens from the area (at 126 in FIG. 10). These images and text data are input into machine learning algorithm 11 at 178, 180, respectively, after the intervening steps of acquiring the data (at 102 in FIGS. 9-10), preparing the data (at 104 in FIGS. 9 and 11 13) and aggregating the data (at 162 in FIG. 12). Training machine learning algorithm 11 at 106 thus also includes labeling the at least one in situ biological image (at 138, 140 in FIG. 10, thereby creating at least one labeled biological image that indicates respective medical condition states shown in each respective biological image. Generally, a plurality of in situ biological images will have been labeled, such that machine learning algorithm 11 receives a plurality of labeled images when the image data is input at 178. Training machine learning algorithm 11 at 106 also includes acquiring patient health data pertaining to the patient from a plurality of data sources (at 130 in FIG. 10), aggregating the patient health data acquired from the plurality of data sources into a text-based (or other format) database (at 162 in FIG. 12), and de-identifying the patient data in the text-based database (at 114 in FIGS. 9 and 13).

Methods of training the machine learning algorithm at 106 also may include selecting relevant features from the text-based database of patient health information, at 182. For example, in some examples, only a subset of the categories of patient health data in the master database will be relevant or needed for a particular type of medical condition state determination. This selection at 182 may be performed by the machine learning algorithm (e.g., as a result of training and thereby learning which features may not be necessary), by the processing unit, and/or manually by a practitioner or other user responsible for preparing and training the machine learning algorithm. Once the relevant features are selected at 182, unnecessary features may be eliminated at 184, such as by removing the unneeded features from the database. Information about the relevant features that were selected at 182 also may be fed back into the system during later de-identification in some examples, as indicated at 172 in FIG. 13. Training the machine learning algorithm at 106 also may include testing, training, and/or validating the algorithm at 186, and finally, deploying the machine learning algorithm at 108. Training and testing the machine learning algorithm at 186 is generally limited to offline learning, though in some examples online learning may be performed by updating the machine learning algorithm's neural network weights, such that the machine learning algorithm continues to learn as it receives additional image input and patient health data during training. In some examples, training and testing the machine learning algorithm at 186 includes splitting, separating, or partitioning, a dataset into three or more subsets to be used in different phases of training the machine learning algorithm. For example, a given dataset may be separated into a training dataset, a testing dataset, and a validation dataset. In this example, training and testing the machine learning algorithm at 186 may include training the machine learning algorithm using the training dataset, testing the machine learning algorithm, using the testing dataset, and validating the machine learning algorithm using the validation dataset. In this manner, different data within a given dataset may used in different phases of training and testing the machine learning algorithm at 186. In a specific example, a majority of a dataset (e.g., greater than 50%, greater than 60%, greater than 70%, and/or greater than 80% of the data in a dataset) may be used as the training dataset, while a smaller proportion of the dataset may be reserved for the testing dataset and for the validation dataset.

Figure 15:
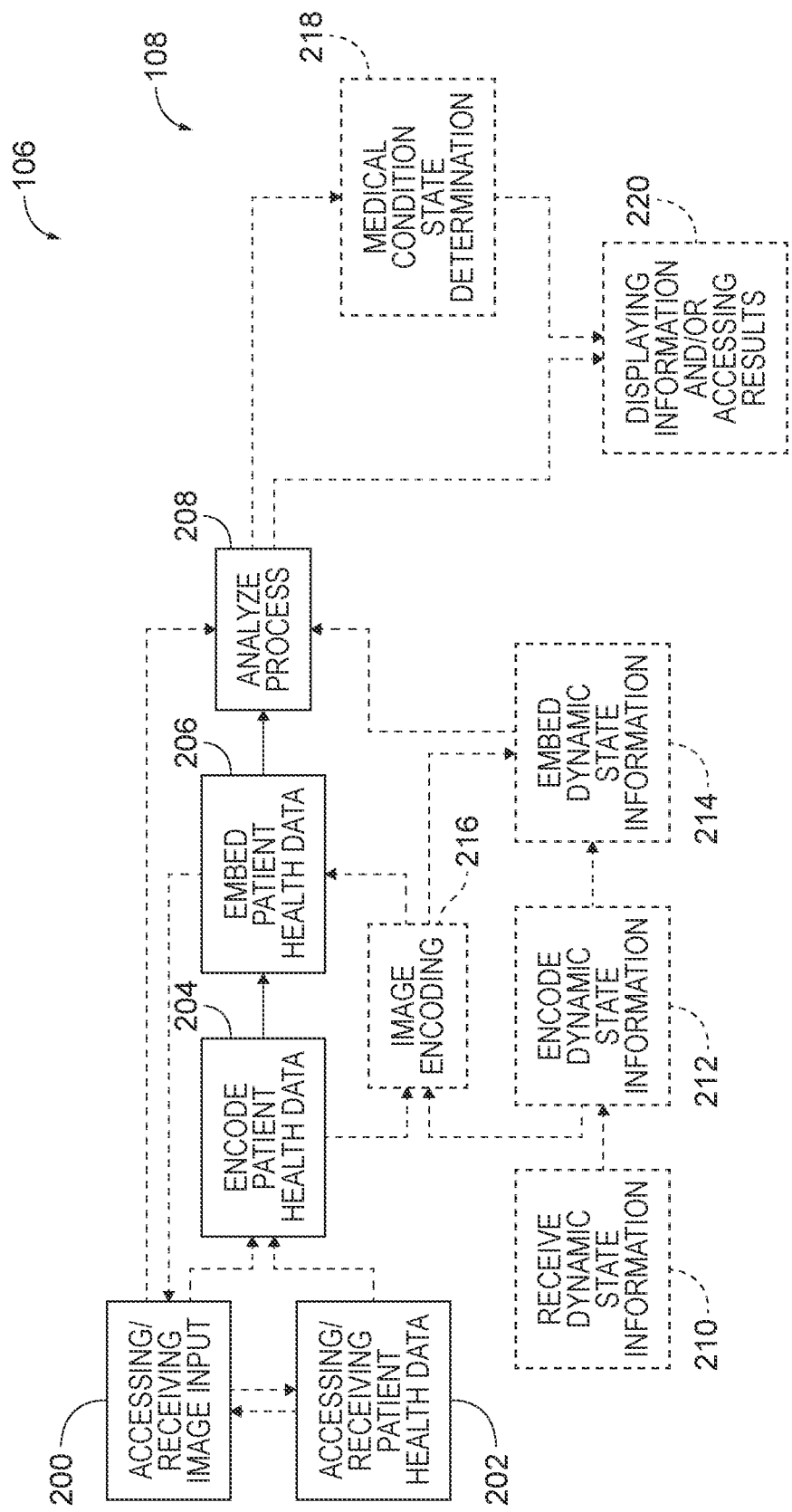
FIG. 15 is a schematic flowchart representation of methods of training and deploying presently disclosed machine learning algorithms for making medical condition state determinations.

FIG. 15 illustrates other methods 106 of training machine learning algorithm 11 to make medical condition state determinations, according to the present disclosure. Examples of training the machine learning algorithm 106 shown in FIG. 15 are not meant to be exclusive, and may overlap with and/or be combined with other methods of training machine learning algorithm 106, described herein. An image input (e.g., image input 14) may be received by at least one processing unit (e.g., processing unit 12) at 200, with the image input being one or more images from an imaging device (e.g., imaging device 16). The at least one processing unit includes the machine learning algorithm stored in one or more memories, though in other examples, the processing unit receiving the image input may be separate from the machine learning algorithm. Receiving the image input at 200 may include receiving labeling information for the image input, such as manual-derived or semi-supervised-derived labeling information (e.g., from 116, 118 in FIGS. 9 and 11).

Methods of training the machine learning algorithm at 106 shown in FIG. 15 also include receiving patient health data (e.g., patient health data 18) as input at 202, with the receiving patient health data at 202 also being performed by the at least one processing unit. In some examples, receiving the patient health data at 202 includes collecting and/or retrieving the patient health data, and delivering the patient health data to the at least one processing unit. For example, a practitioner may collect and enter patient health data at 202 from a chart or medical records, from asking the patient for information, and then entering or inputting the patient health data into the processing unit. In some examples, collecting and/or retrieving the patient health data may be performed in real-time. For example, patient health data may be obtained and entered during a colonoscopy procedure, such as by asking a patient questions during the procedure. Additionally or alternatively, collecting and/or retrieving patient health data may be performed before the procedure (e.g., before the colonoscopy), and therefore before receiving image input for analysis by the machine learning algorithm. For example, patient health data collected and stored in medical records generally will have been collected prior to the medical procedure, and may be accessed before or during the procedure and input to the machine learning algorithm. In various examples, patient health data received and/or collected at 202 may include survey question answers, static data, electronic health records, electronic medical records, demographic information, medications, drug use, smoking history, computed risk predictors, blood work, prior procedural results, and/or risk factors. As specific examples, patient health data collected and/or received at 202 may include body mass index (BMI), physical activity, cigarette smoking history, alcohol usage, family history, inflammatory bowel disease, current hormone therapy (e.g., postmenopausal hormone therapy), former hormone therapy (e.g., postmenopausal hormone therapy), aspirin usage, nonsteroidal anti-inflammatory drugs (NSAIDs) usage, consumption of processed and/or red meat, fruit and vegetable consumption levels, demographic information, medications, drug usage, diet type and quality, dietary fat intake, weight, height, age, race, presence of other illnesses, biological markers, INR/PTT/PT/platelets/bleed time, previous endoscopy results, previous CT scan results, previous angiogram information, previous MRI results, and/or previous sonography data.

In some examples, receiving the patient health data at 202 may include de-identifying the patient health data (e.g., at 114 from FIGS. 9 and 13). Said data de-identification generally will be performed during the training the machine learning algorithm at 106, and are optional during the deploying the machine learning algorithm at 108. In other words, patient health data input into the machine learning algorithm may be de-identified if the data is being used to train the machine learning algorithm, but patient-identifying information may be retained in association with the patient health data when the machine learning algorithm is deployed to make a medical condition state determination for a particular patient. There may be some examples where it is desired to train the machine learning algorithm using data that has not been de-identified, or where it is desired to de-identify the data during deployment of the machine learning algorithm as well.

Training the machine learning algorithm 106 also may include encoding the patient health data at 204, thereby converting the patient health data to encoded patient health data (e.g., encoded patient health data 20). The encoding the patient health data and converting the patient health data at 204 is performed by the at least one processing unit, according to instructions stored on the processing unit. The encoded patient health data is then embedded into at least one image of the image input, at 206. Thus, disclosed systems are configured such that the machine learning algorithm is informed and trained using both training images (e.g., image input) and patient health training data that is encoded such that it may be added to, appended to, overlaid on, and/or embedded in the image training data.

In some examples, embedding the encoded patient health data at 206 includes embedding the encoded patient health data within a consistent region of the at least one image, such as described in connection with FIGS. 7-8. The embedding the encoded patient health data is performed by the at least one processing unit, wherein the machine learning algorithm is configured to make a medical condition state determination based on the image input and the encoded patient health data. To do so, the image input and the embedded patient health data is input to (and received by) the machine learning algorithm for analysis and processing at 208. In some examples, the encoded patient health data is input into a fully connected network portion of the machine learning algorithm. The machine learning algorithm thus may be trained at 106 using this encoded and embedded patient health data, along with the image input.

Training and preparing the machine learning algorithm at 106 in FIG. 15 also may be understood from the perspective of programming the processing unit to perform the steps described above. For example, receiving the image input at 200 may include programming at least one processing unit (e.g., processing unit 12) to receive an image input (e.g., image input 14), with the image input being one or more images from an imaging device (e.g., imaging device 16), and with the machine learning algorithm being stored within a memory of the processing unit. In other examples, the machine learning algorithm may be accessed by the processing unit, rather than stored therein. Similarly, receiving the patient health data at 202 may include programming the processing unit to receive patient health data as input, and encoding the patient health data at 204 may include programming the at least one processing unit to encode the patient health data and thereby convert the patient health data to encoded patient health data. Embedding the encoded patient health data at 206 may include programming the processing unit to embed the encoded patient health data into at least one image of the image input. In this manner, the processing unit may be programmed such that it is configured to make a medical condition state determination, via the machine learning algorithm, based on the image input and the encoded patient health data.

Once trained, the machine learning algorithm may be deployed at 108 according to the same methods, where image input is received at 200, patient health data is received at 202, the patient health data is encoded at 204 and embedded at 206, and then input to the machine learning algorithm for analysis and processing at 208, to thus make a medical condition state determination using the image input and patient health data. Thus, FIG. 15 may represent methods of training the machine learning algorithm at 106 and methods of deploying the machine learning algorithm at 108. In the deploying at 108, receiving the image input at 200 may include accessing an image input by the machine learning algorithm, again with the image input being one or more images from an imaging device used to perform a medical imaging procedure on a patient. Similarly, receiving the patient health data at 202 may include accessing and/or retrieving patient health data with the machine learning algorithm. Accessing and/or retrieving the patient health data at 202 may be performed in real-time, and/or may include accessing or retrieving patient health data that was collected or provided before the accessing the image input at 200 (e.g., before the medical procedure). Analyzing and processing the image input and encoded patient health data at 208 may include causing the machine learning algorithm to analyze the image input and the patient health data together to make the medical condition state determination. In such methods, the machine learning algorithm may be configured to encode the patient health data to convert the patient health data to encoded patient health data at 204, and/or such encoding at 204 may be performed by the processing unit. Similarly, the embedding the encoded patient health data at 206 may be performed by the machine learning algorithm and/or by the processing unit. The machine learning algorithm makes a medical condition state determination at 218, based on its analyzing and processing of the image input and encoded patient health data at 208. The analysis results (e.g., the medical condition state determination) produced by the machine learning algorithm may be accessed at 220, such as via the output image displayed at 220, which serves as a visual representation of the encoded patient health data viewable on the analysis results, all together as a single source (e.g., visual output augmented with encoded patient health data and the medical condition state determination in the output image). While prior art machine learning models were not able to provide visualization of data from multiple sources to a physician or other practitioner, currently disclosed machine learning algorithms 11 are able to provide this functionality.

In training the machine learning algorithm at 106 and/or deploying the machine learning algorithm at 108, the encoded patient health data may be embedded into the at least one image of the image input at 206 at or before a time that the machine learning algorithm analyzes and processes the image input at 208, such that the machine learning algorithm analyzes the image input together with the encoded patient health data embedded in the at least one image of the image input. In other words, the machine learning algorithm may be trained to analyze the patient health data integrally with the image input being analyzed. In various examples of training at 106 and deploying at 108, encoding the patient health data at 204 and/or encoding dynamic state information at 212 (discussed below) may include performing a one-hot encoding conversion and/or performing data dictionary encoding. Additionally or alternatively, encoding the patient health data at 204 may include converting the patient health data to a plurality of collections of coded image pixels (e.g., collection of coded image pixels 34) that are added to, appended to, overlaid on, and/or embedded in the at least one image of the image input.

In some examples, embedding the patient health data at 206 may include adding, appending, and/or overlaying the encoded patient health data to the image input as a vector and/or a data tensor (though as used herein, a "vector" is a subset of, or type of, tensor (also known as a "data tensor"), wherein the adding, appending, and/or overlaying generally being performed by the at least one processing unit. Additionally or alternatively, the encoded patient health data may be added, appending, and/or overlaid onto a data tensor. Encoding the patient health data at 204 may include selectively representing the patient health data and/or dynamic state information as a tensor and/or as a plurality of collections of coded image pixels, in various examples of presently disclosed systems.

Some examples of methods of training the machine learning algorithm at 106 and/or deploying the machine learning algorithm at 108 include performing similar steps with dynamic state information (e.g., dynamic state information 48), in addition to the patient health data. For example, dynamic state information may be received by the processing unit at 210 (e.g., from one or more dynamic state apparatus 46 configured to deliver said dynamic state information as additional input), encoded at 212 to form encoded dynamic state information (e.g., encoded dynamic state information 49), and embedded into the at least one image of the image input at 214, at or before a time that the machine learning algorithm analyzes the image input. In this manner, the encoded dynamic state information also may be input to the machine learning algorithm, such that the machine learning algorithm may analyze the image input together with the encoded dynamic state information (and the encoded patient health data) embedded in the at least one image of the image input, at 208. In some examples, the encoded dynamic state information is input into a fully connected network portion of the machine learning algorithm during the analyzing at 208. In some examples, embedding the encoded dynamic state information at 214 includes adding, appending, and/or overlaying encoded dynamic state information to the image input as a vector and/or a data tensor, with the appending generally being performed by the at least one processing unit.

In some examples, the encoded patient health data may be embedded into the image input at 206 before the image input is received by the processing unit at 200. In other words, a processing unit other than the processing unit that includes the machine learning algorithm may perform the encoding at 204 and/or the embedding at 206, in some examples. Similarly, and additionally or alternatively, the encoded dynamic state information may be embedded into the image input at 214 before the image input is received by the processing unit at 200, such as in examples where a processing unit other than the processing unit that includes the machine learning algorithm performs the encoding at 212 and/or the embedding at 214.

Some examples of methods of training the machine learning algorithm at 106 and/or deploying the machine learning algorithm at 108 include image encoding the encoded patient health data and/or image encoding the encoded dynamic state information at 216, which may be performed by the processing unit after encoding the patient health data at 204. Additionally or alternatively, methods 106, 108 may include image encoding the dynamic state information at 216, which may be performed by the processing unit after encoding the dynamic state information at 212. Image encoding the encoded patient health data and/or the encoded dynamic state information at 216 may include adding, overlaying, and/or appending image pixels to the image input. Said image encoding at 216, if performed, is performed prior to inputting the image input to the machine learning algorithm for analysis and processing at 208. In some examples, the image encoding at 216 may be performed prior to the receiving the image input at 200, such as in examples where a different processing unit performs the image encoding than the processing unit that includes the machine learning algorithm.

Methods of training the machine learning algorithm at 106 and/or deploying the machine learning algorithm at 108 include making a medical condition state determination at 218, such as by detecting, classifying, and/or localizing a feature of interest in one or more image inputs based on the image input and the encoded patient health data. Making the medical condition state determination generally includes processing and interpreting the encoded patient health data along with the image input itself. Again, the encoded patient health data is embedded in at least one image of the image input, such as in the form of a plurality of collections of coded image pixels added to the image input. Making the medical condition state determination at 218 may be performed in real time. In other words, disclosed machine learning algorithms may be used to make medical condition state determinations while the medical procedure is being performed to produce the image input, with said medical condition state determination being based on the image input and the encoded patient health data. For example, images from a colonoscopy procedure may be sent to the machine learning algorithm during the colonoscopy, and the machine learning algorithm may be configured to detect, classify, and/or localize polyps and/or other medical condition states or features in real-time during the colonoscopy procedure or other medical procedure. Making a medical condition state determination at 218 generally will be an automated determination, or at least a semi-automated determination, by the machine learning algorithm. Furthermore, making the medical condition state determination at 218 may include determining a probabilistic diagnosis (e.g., a confidence level, which may be expressed in the form of a percentage) of the medical condition state of the image input, via the machine learning algorithm, and/or any additional relevant information, such as the information discussed above in connection with FIGS. 3-6.

Methods of training the machine learning algorithm at 106 and/or deploying the machine learning algorithm at 108 may include accessing the results and/or displaying information (e.g., the medical condition state determination) at 220 after the machine learning algorithm has analyzed the image input, the encoded patient health information, and/or the dynamic state information to make the medical condition state determination. For example, displaying information at 220 may include producing and displaying an output image (e.g., output image 40) on a display device (e.g., display device 42), which generally will show the image input that includes the medical condition that was detected by the machine learning algorithm (e.g., visual output for the medical condition state determination), information about the medical condition state determination (e.g., diagnosis and confidence in the determination), along with at least some relevant patient health data pertaining to the medical condition state determination (e.g., encoded patient health data 20). In this manner, disclosed systems produce and display output images at 220 that show visual output that is augmented with encoded patient health data. Producing the output image at 220 may be performed by the machine learning algorithm and/or by the processing unit (e.g., an encoding algorithm of processing unit 12) described in connection with disclosed systems 10. In some examples, displaying information at 220 includes displaying the encoded patient health data within a consistent region of an output image (e.g., within a given region 32), wherein the displaying is performed by, or instructed by, the at least one processing unit. In some examples, displaying information at 220 includes displaying real-time patient health history data. In some examples, displaying information at 220 includes displaying the encoded patient health data via labels and/or icons (e.g., icons 44).

Figure 16:
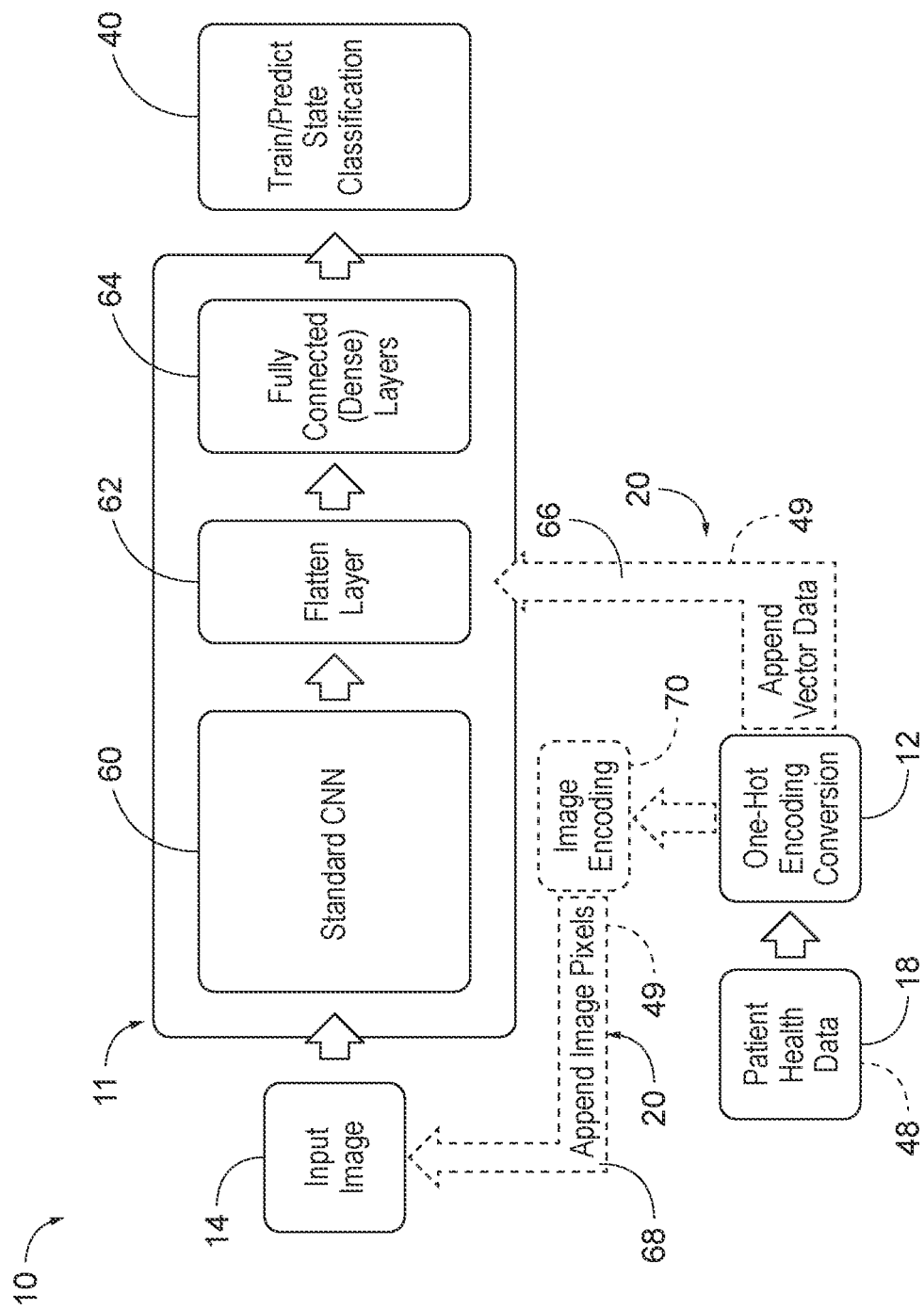
FIG. 16 is a schematic representation of non-exclusive examples of machine learning algorithm architectures that may be employed in presently disclosed systems.
Figure 17:
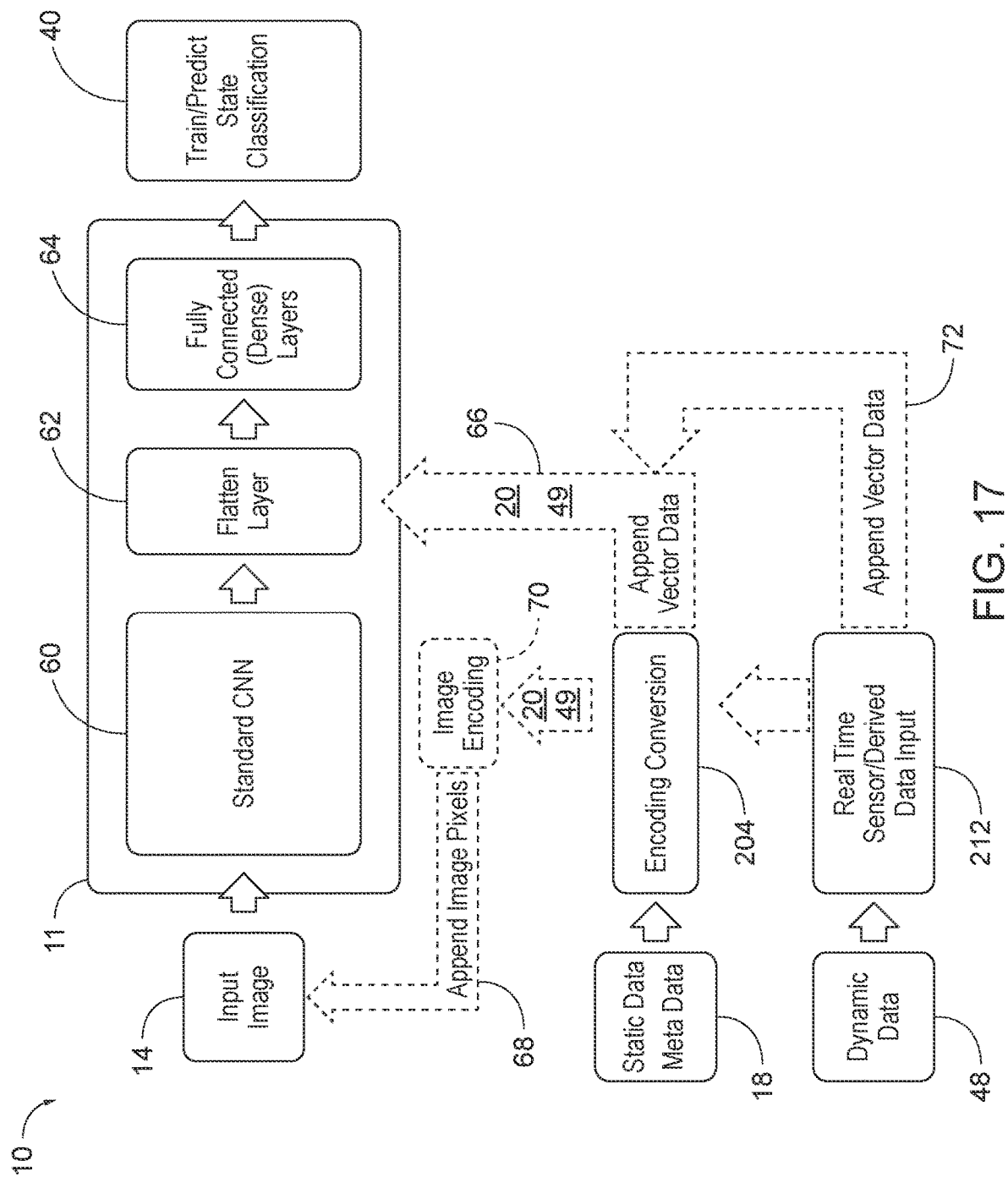
FIG. 17 is a schematic representation of non-exclusive examples of machine learning algorithm architectures that may be employed in presently disclosed systems.

Turning now to FIGS. 16-17, the architecture and operation of examples of machine learning algorithms 11 according to the present disclosure are described. As shown, in one example of machine learning algorithm 11, image inputs 14 are input into machine learning algorithm 11, such as to a standard convolutional neural network 60 of machine learning algorithm 11. Standard convolutional neural network 60 may be fully trained with randomly initialized weights, or may be a transfer learning neural network with pre-trained weights. In some examples, transfer learning can enable machine learning algorithm 11 to be trained using smaller images and/or less data, though fully trained models on larger datasets with medically relevant images may be more accurate for real-time medical condition state determinations according to the present disclosure. Machine learning algorithm 11 may include a reshaping layer 62 and one or more fully connected (dense) layers 64. In various examples of systems 10, patient health data 18 may input into machine learning algorithm 11 at one or more different points. For example, processing unit 12 may perform an encoding operation on patient health data 18 (which may be a one-hot encoding conversion, and/or a different type of encoding) to produce encoded patient health data 20. In some examples, encoded patient health data 20 may be input into machine learning algorithm 11 by inputting encoded patient health data 20 directly into neural network 60, as indicated by arrow 66. Additionally or alternatively, encoded patient health data 20 may be input into machine learning algorithm 11 along with image input 14, as indicated by arrow 68. Similarly, encoded dynamic state information 49 may be input into machine learning algorithm 11 by inputting encoded dynamic state information 49 directly into neural network 60, also as indicated by arrow 66, and/or encoded dynamic state information 49 may be input into machine learning algorithm 11 along with image input 14, as also indicated by arrow 68.

In some examples, this process involves adding (e.g., appending, overlaying, and/or embedding) encoded patient health data 20 and/or encoded dynamic state information 49 to image input 14 as a vector or data tensor (arrow 66). For example, processing unit 12 may be programmed to add encoded patient health data 20 to image input 14 as a vector after image input 14 is reshaped (e.g., flattened) and/or concatenated, as represented by reshaping layer 62. For example, the reshaping operation may be configured to convert tensor data into vector data and then added (e.g., appended and/or concatenated) to image input 14 within the layers of machine learning algorithm 11 and/or added to image input 14 before being input into machine learning algorithm 11. Similarly, encoded dynamic state information 49 also may be appended to image input 14 as a vector or data tensor, such that processing unit 12 may be configured to add encoded dynamic state information to the image input as the vector or the data tensor after the image input is reshaped (e.g., flattened) and/or concatenated. In other words, processing unit 12 may be configured to embed encoded patient health data 20 and/or encoded dynamic state information 49 into a tensor of machine learning algorithm 11. In some examples, vector data representing encoded patient health data 20 and/or encoded dynamic state information 49 may be added to image input within a fully connected network portion of machine learning algorithm 11 (e.g., adding the vector to fully connected layers 64).

In examples that include inputting encoded patient health data 20 and/or encoded dynamic state information 49 with image input 14 (arrow 68), collections of coded images pixels (e.g., collection of coded image pixels 34) may be appended to image input 14 before image input 14 is input to machine learning model 11, as indicated by arrow 68. In some examples, image encoding is performed (indicated at 70) before the image pixels are appended to image input 14. Image encoding at 70 may include overwriting pixels on top of the original image input and/or expanding the image size or resolution, such as by adding pixels to the border.

FIG. 17 illustrates similar examples of system 10 with small variations. In some examples represented in FIG. 17, patient health data 18 (which may be static data and/or meta-data) is encoded at 204, thereby being converted to encoded patient health data 20, and dynamic state information 48 is encoded at 212, thereby being converted to encoded dynamic state information 49, which may be real-time sensor-derived data input. In some examples, encoded patient health data 20 and/or encoded dynamic state information 49 is input into machine learning algorithm 11 by appending vector data to the image input (which may have been reshaped into a tensor) within the neural network (as indicated by arrows 66 and 72). In these examples, machine learning algorithm 11 may be a custom, or atypical, convolutional neural network architecture. Additionally or alternatively, encoded patient health data 20 and/or encoded dynamic state information 49 is optionally subjected to image encoding at 70 and embedded into image input 14 prior to the image input being input to the neural network, such as by appending image pixels to image input 14 (indicated by arrow 68). In these examples, machine learning algorithm 11 may be a generic, or standard, neural network.

Figure 18:
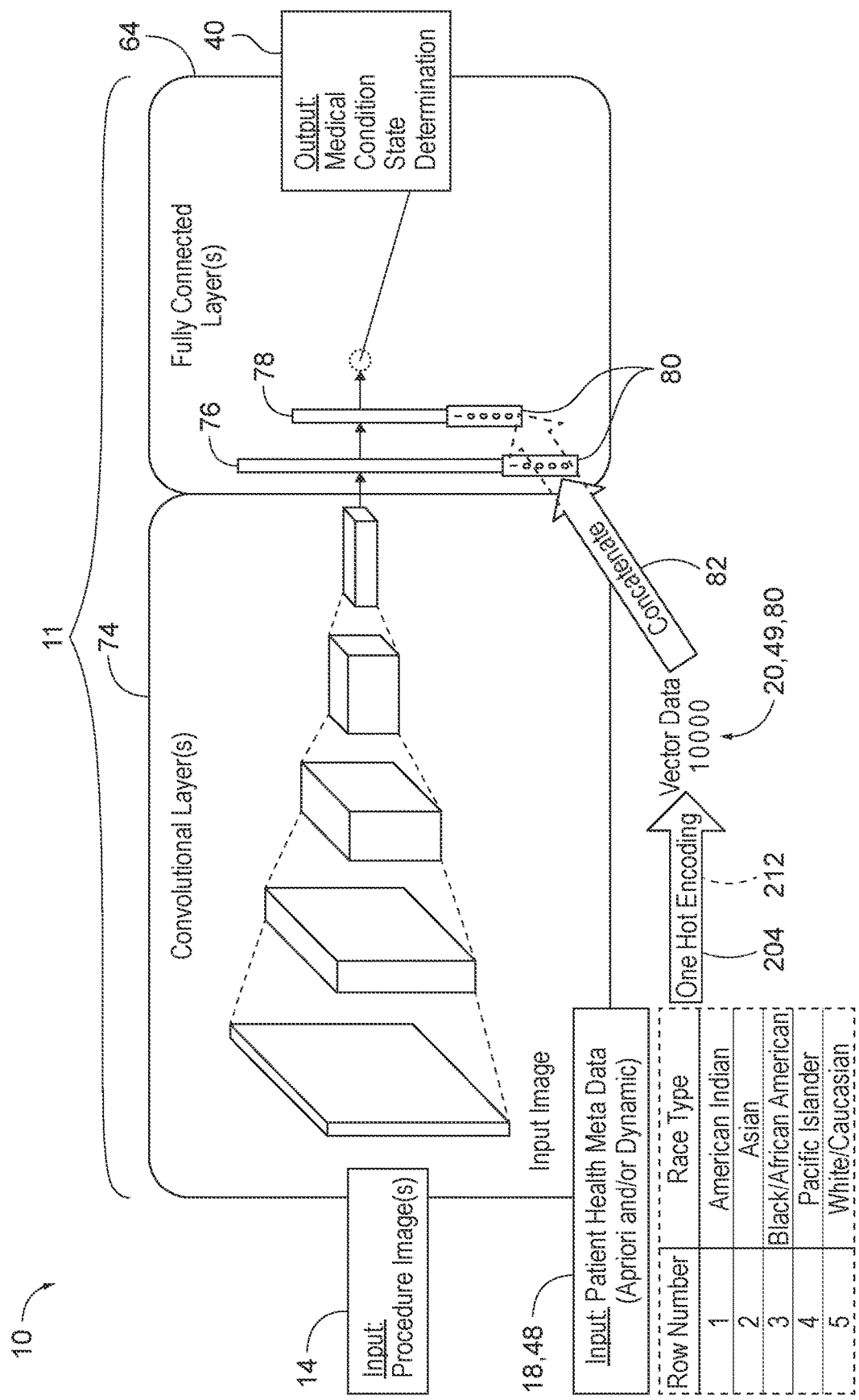
FIG. 18 is another schematic representation of non-exclusive examples of machine learning algorithm architectures that may be employed in presently disclosed systems.

FIG. 18 shows another view of examples of machine learning algorithm 11 of systems 10. As shown in FIG. 18, machine learning algorithm may include one or more convolutional layers 74 and one or more fully connected layers 64. As with other examples of system 10, one or more image inputs 14 are input into machine learning algorithm 11. Each convolutional layer 74 may transform, or reshape, dimensions of image input 14, until the image is reshaped (e.g., flattened) into a tensor 76 or a vector 76 to be operated on in subsequent fully connected layers 64. Tensor 76 may be transformed into one or more other tensors 78 from within the fully connected layer(s) 64 of the neural network before output image 40 is produced with the medical condition state determined by machine learning algorithm 11. As shown in other examples, patient health data 18 and/or dynamic state information 48 may be reshaped and/or encoded at 204 and/or 212 to produce vector data 80, which represents an example of encoded patient health data 20 and/or encoded dynamic state information 49. Said vector data 80 may be added to tensor 76 or tensor 78 (which are tensor representations of image input 14) by a concatenation operation indicated at 82. In some examples of system 10, concatenation 82 occurs before passing data from convolutional layers 74 into fully connected layers 64 and after flattening or a reshape operation such that the tensor dimensionality matches to permit a concatenation operation.

In some examples of system 10, concatenation 82 occurs within fully connected layers 64, as represented by vector data 80 being shown concatenated on tensor 76 and tensor 78. This concatenation 82 occurs before machine learning algorithm 11 makes a medical condition state determination and before output image 40 is produced, such that machine learning algorithm 11 is informed by both image input 14 (which has been converted to the form of tensors 76, 78) and encoded patient health data 20, which is encoded as vector data 80 concatenated onto tensors 76,78 within fully connected layers 64. The machine learning algorithm 11 makes a medical state determination and is then passed to an output image rendering function which facilitates creation of a composite image (e.g., output image 40) which will visualize the medical state determination state information in the desired configuration and which may be rendered on a display device (e.g., display device 42), as described in detail herein. Output image 40 may include information about the classification, localization, and/or confidence level of the medical condition state determination made by machine learning algorithm 11. For example, output image 40 may display a bounding box (e.g., bounding box 36) with a box width, box height, and/or a classification and associated confidence level. Saud output image 40 may be rendered (e.g., by image display rendering function 41), displayed (e.g., on display device 42), printed, and/or at least partially communicated via auditory signals in various examples according to the present disclosure.

Illustrative, non-exclusive examples of inventive subject matter according to the present disclosure are described in the following enumerated paragraphs:

A1. A system for preparing, training, and deploying a machine learning algorithm for making a medical condition state determination, the system comprising:
at least one processing unit comprising the machine learning algorithm, wherein the machine learning algorithm is stored in one or more memories of the at least one processing unit, wherein the at least one processing unit is programmed to:
receive an image input from an imaging device, wherein the image input comprises one or more images obtained and/or produced by the imaging device;
receive patient health data as input;
encode the patient health data to convert the patient health data to encoded patient health data; and
transmit the encoded patient health data into the machine learning algorithm,
wherein the system is configured to make the medical condition state determination based on the image input and the encoded patient health data, via the machine learning algorithm.

A1.1 The system of paragraph A1, wherein the system is configured such that the encoded patient health data is embedded into at least one image of the image input at or before a time that the machine learning algorithm analyzes the image input, such that the machine learning algorithm analyzes the image input together with the encoded patient health data embedded in the at least one image of the image input.

A1.2. The system of paragraph A1 or A1.1, further comprising the imaging device, wherein the imaging device is configured to produce the one or more images.

A1.3. The system of any of paragraphs A1-A1.2, wherein the machine learning algorithm comprises a convolutional neural network.

A1.4. The system of any of paragraphs A1-A1.3, wherein the machine learning algorithm comprises a transformer, an LS™, an RNN, an SVM, a dense neural network, an auto-encoder, and/or a YOLO.

A1.5. The system of any of paragraphs A1-A1.4, wherein the at least one processing unit is configured to receive the patient health data as an input tensor.

A1.6. The system of any of paragraphs A1-A1.5, wherein the at least one processing unit is further configured to receive a sound input, an NIR input, sensor measurement data, 2D vector data, 3D vector data, and/or 4D vector data.

A1.7. The system of any of paragraphs A1-A1.6, wherein the at least one processing unit is configured to embed the encoded patient health data into at least one image of the image input.

A1.8. The system of any of paragraphs A1-A1.7, wherein the at least one processing unit is configured to embed the encoded patient health data into a tensor of the machine learning algorithm.

A1.9. The system of any of paragraphs A1-A1.8, wherein the machine learning algorithm is trained using one or more selected from the group consisting of unsupervised learning, semi-supervised learning, and supervised learning.

A2. The system of any of paragraphs A1-A1.9, wherein the machine learning algorithm comprises a fully trained convolutional neural network.

A3. The system of any of paragraphs A1-A2, wherein the machine learning algorithm comprises a transfer learning convolutional neural network.

A4. The system of any of paragraphs A1-A3, wherein the at least one processing unit is further programmed to perform one-hot encoding conversion to encode the patient health data and thereby convert the patient health data to the encoded patient health data.

A5. The system of any of paragraphs A1-A4, wherein the system further comprises a one-hot encoding system configured to convert data concerning patient risk factors into a numerical representation based on a predefined data schema, thereby converting the patient health data to the encoded patient health data.

A6. The system of paragraph A4 or A5, wherein the at least one processing unit is further programmed to image encode the patient health data after one-hot encoding conversion of the patient health data.

A7. The system of any of paragraphs A1-A6, wherein the at least one processing unit is further programmed to perform a reshaping and/or concatenating operation to reshape, flatten, and/or concatenate the encoded patient health data and/or at least one image of the image input.

A8. The system of any of paragraphs A1-A7, wherein the system is configured to display the encoded patient health data within a region of at least one image of the image input.

A8.1. The system of any of paragraphs A1-A8, wherein the system is configured to embed the encoded patient health data within a region of at least one image of the image input.

A9. The system of any of paragraphs A1-A8.1, wherein the encoded patient health data comprises a plurality of collections of coded image pixels that are added to the image input.

A9.1. The system of paragraph A9, wherein the plurality of collections of coded image pixels are appended to the image input.

A9.2. The system of paragraph A9, wherein the plurality of collections of coded image pixels are overlaid onto the image input.

A10. The system of any of paragraphs A1-A9.2, wherein the at least one processing unit is further programmed to add the encoded patient health data to the image input as a vector and/or a data tensor.

A10.1. The system of any of paragraphs A1-A10, wherein the at least one processing unit is further programmed to add dynamic state information to the image input as a/the vector and/or a/the data tensor.

A10.2. The system of any of paragraphs A1-A10.1, wherein the at least one processing unit is configured to append the encoded patient health data to a/the data tensor.

A11. The system of paragraph A10 or A10.1, wherein the at least one processing unit is further programmed to add the encoded patient health data to the image input as the vector or the data tensor after the image input is reshaped and/or concatenated.

A11.1. The system of any of paragraph A10-A11, wherein the at least one processing unit is further programmed to add encoded dynamic state information to the image input as the vector and/or the data tensor after the image input is reshaped and/or concatenated.

A12. The system of any of paragraphs A1-A11.1, wherein the system is configured to selectively represent the patient health data as a/the tensor and/or a/the plurality of collections of coded image pixels.

A13. The system of any of paragraphs A1-A12, wherein the machine learning algorithm is configured to receive the encoded patient health data into a fully connected network portion of the machine learning algorithm.

A14. The system of any of paragraphs A1-A13, wherein the system is configured to perform real-time medical condition state determination.

A14.1. The system of any of paragraphs A1-A14, wherein the system is configured to perform automated medical condition state determination.

A14.2. The system of any of paragraphs A1-A14.1, wherein the system is configured to automatically generate a report for a/the patient that includes a summary of the medical condition state determination, along with billing information for the procedure.

A15. The system of any of paragraphs A1-A14.2, further comprising a computing device configured for collecting and/or retrieving the patient health data, wherein the computing device is further configured to deliver the patient health data to the at least one processing unit.

A16. The system of paragraph A15, wherein the computing device is configured to collect and/or retrieve the patient health data in real-time from a database.

A16.1. The system of paragraph A16, wherein the database comprises electronic health records and/or electronic medical records.

A16.2. The system of any of paragraphs A1-A16.1, wherein the patient health data is collected or provided before the image input is provided to the at least one processing unit.

A17. The system of any of paragraphs A1-A16.2, wherein the patient health data comprises survey question answers, static data, active data, the electronic health records, the electronic medical records, and/or risk factors.

A17.1. The system of any of paragraphs A1-A17, wherein the patient health data comprises body mass index (BMI), physical activity, cigarette smoking history, alcohol usage, family history, presence of inflammatory bowel disease, current hormone therapy (e.g., postmenopausal hormone therapy), former hormone therapy (e.g., postmenopausal hormone therapy), aspirin usage, nonsteroidal anti-inflammatory drugs (NSAIDs) usage, consumption of processed and/or red meat, fruit and vegetable consumption levels, demographic information, medications, drug usage, diet type and quality, dietary fat intake, weight, height, age, race, presence of other illnesses, biological markers, INR/PTT/PT/platelets/bleed time, previous endoscopy results, previous CT scan results, previous angiogram information, previous MRI results, computed risk predictors, blood work, prior procedural results, and/or previous sonography data.

A18. The system of any of paragraphs A1-A17.1, wherein the machine learning algorithm is configured to detect one or more medical condition states based on the one or more images and the patient health data.

A18.1. The system of any of paragraphs A1-A18, wherein the system is configured to display the one or more medical condition states and/or the patient health data.

A18.2. The system of paragraph A18.1, wherein the system is configured to display the one or more medical condition states and/or the patient health data using a bounding box, text, a shaped outline, a visual indication on a screen or monitor, and/or an auditory signal.

A19. The system of any of paragraphs A1-A18.2, wherein the machine learning algorithm is configured to classify a/the one or more medical condition states based on the one or more images and the patient health data.

A20. The system of any of paragraphs A1-A19, wherein the machine learning algorithm is configured to localize a/the one or more medical condition states based on the one or more images and the patient health data.

A21. The system of any of paragraphs A1-A20, wherein the at least one processing unit is configured to perform de-identification of the patient health data.

A22. The system of any of paragraphs A1-A21, wherein the at least one processing unit is configured to receive manual labeling information for the image input.

A23. The system of any of paragraphs A1-A22, wherein the at least one processing unit is configured to receive semi-supervised labeling information for the image input.

A23.1. The system of any of paragraphs A1-A23, wherein the at least one processing unit is configured to first receive the supervised labeling information, and then to receive the semi-supervised labeling information, and then to perform auto-labeling.

A23.2. The system of any of paragraphs A1-A23.1, wherein the at least one processing unit is configured to first receive the supervised labeling information and/or to perform auto-labeling, and then to receive the semi-supervised labeling information to refine and improve labels in a dataset.

A24. The system of any of paragraphs A1-A23.2, wherein the system is configured to perform a labeling feedback loop comprising the semi-supervised labeling information.

A24.1. The system of paragraph A24, wherein the labeling feedback loop improves training efficiency of the machine learning algorithm.

A24.2. The system of paragraph A24 or A24.1, wherein the labeling feedback loop enables the machine learning algorithm to be trained using large scale data and/or big data.

A25. The system of any of paragraphs A1-A24.2, wherein the system is configured to receive large scale data and/or big data for training the machine learning algorithm.

A26. The system of any of paragraphs A1-A25, wherein the machine learning algorithm comprises a custom convolutional neural network.

A27. The system of any of paragraphs A1-A26, wherein the system is configured such that the machine learning algorithm is informed and trained using both image training data and patient health training data that is encoded such that it may be appended to, added to, overlaid on, and/or embedded in the image training data.

A28. The system of any of paragraphs A1-A27, wherein the system is configured to provide visual output for medical condition state determination via a graphical user interface, wherein the visual output is augmented with the patient health data.

A29. The system of any of paragraphs A1-A28, wherein the patient health data comprises information regarding a patient's cardiac cycle and/or breathing cycle, and wherein the image input is temporally annotated such that each of the one or more images from the imaging device may be matched with a phase of the patient's cardiac cycle and/or breathing cycle.

A30. The system of any of paragraphs A1-A29, wherein the at least one processing unit comprises an encoding algorithm configured to produce an output image that comprises at least one image of the image input and the encoded patient health data.

A30.1. The system of paragraph A30, further comprising a display configured to display the output image.

A30.2. The system of paragraph A30 or A30.1, wherein the output image comprises a printed output image and/or a digital output image.

A31. The system of any of paragraphs A30-A30.2, wherein the output image further comprises the medical condition state determination determined by the machine learning algorithm.

A32. The system of any of paragraphs A1-A31, wherein the system is configured for online learning such that the machine learning algorithm is updated using neural network weights, and thereby continues to learn as it receives additional image input and additional patient health data.

A33. The system of any of paragraphs A1-A32, wherein the imaging device comprises an sonography device, an x-ray device, a computed tomography (CT) scanning device, a magnetic resonance imaging (MRI) device, a positron emission tomography (PET) device, a retinal camera, a dermatoscope, a radiograph device, a mammography device, an endoscope, a colonoscopy device, an esophagogastroduodenoscopy device, a bronchoscopy device, a photoacoustic endoscopy device, an electro-optical sensor, a NBI (Narrow Band Imaging) colonoscopy device, a white light endoscopy device, a chromoendoscopy device, and/or a capsule endoscopy device.

A34. The system of any of paragraphs A1-A33, further comprising an apparatus for determining dynamic state information of a patient, wherein the apparatus is configured to deliver the dynamic state information to the at least one processing unit as an additional input.

A34.1. The method of paragraph A34, wherein the dynamic state information comprises heart rate, blood pressure, compensated heart rate, anesthetics, telemetry, saline used, oxygen saturation, end tidal carbon dioxide (capnography), current medications, and/or activity in distal extremities.

A34.2. The method if paragraph A34 or A34.1, wherein the apparatus comprises one or more motion sensors, one or more accelerometers, and/or one or more video cameras configured for motion detection.

A34.3. The system of any of paragraphs A1-A34.2, wherein the system is configured such that dynamic state information is embedded into at least one image of the image input at or before a time that the machine learning algorithm analyzes the image input, such that the machine learning algorithm analyzes the image input together with the dynamic state information embedded in the at least one image of the image input.

A34.4. The system of any of paragraphs A1-A34.3, wherein the at least one processing unit is further programmed to perform one-hot encoding conversion to encode the dynamic state information.

A34.5. The system of paragraph A34.4, wherein the at least one processing unit is further programmed to image encode the dynamic state information after one-hot encoding conversion of the dynamic state information.

A34.6. The system of any of paragraphs A1-A34.5, wherein the machine learning algorithm is configured to receive the encoded dynamic state information into a/the fully connected network portion of the machine learning algorithm.

A35. The system of any of paragraphs A1-A34.6, wherein the machine learning algorithm is configured to process and interpret encoded patient health data that is embedded in at least one image as a/the plurality of collections of coded image pixels.

A35.1. The system of paragraph A35, wherein the plurality of collections of coded image pixels comprises a respective collection of coded image pixels for each respective type or category of encoded patient health data.

A35.2. The system of paragraph A35 or A35.1, wherein the plurality of collections of coded image pixels are arranged in a row, a column, and/or an array on the at least one image.

A35.3. The system of any of paragraphs A35-A35.2, wherein the plurality of collections of coded image pixels are positioned together within a given region of the at least one image.

A35.4. The system of any of paragraphs A35-A35.3, wherein a respective shade of each respective collection of coded image pixels represents the relative value of the respective encoded patient health data encoded in the respective collection of coded image pixels.

A36. The system of any of paragraphs A1-A35.4, wherein the plurality of collections of coded image pixels comprises a plurality of collections of grayscale-coded image pixels.

A36.1. The system of any of paragraphs A1-A36, wherein the plurality of collections of coded image pixels comprises a plurality of collections of color-coded image pixels.

A37. The system of any of paragraphs A35-A36.1, wherein the system is configured to display a respective icon for each respective collection of coded image pixels to indicate what the respective collection of coded image pixels is encoding.

A38. The system of any of paragraphs A1-A37, wherein the machine learning algorithm is configured to determine a probabilistic diagnosis of a/the medical condition state of the image input, based on the image input and the encoded patient health data.

A39. The system of any of paragraphs A1-A38, wherein the machine learning algorithm is between 1 and 15 layers deep.

B1. A method of training and preparing a machine learning algorithm for medical condition state determination, the method comprising:
    acquiring data from at least one medical procedure, wherein the acquiring data comprises acquiring at least one in situ biological image of an area of a patient's body and acquiring one or more biological specimens from the area;
    labeling the at least one in situ biological image, thereby creating at least one labeled biological image that indicates respective medical condition states shown in each respective biological image;
    acquiring patient health data pertaining to the patient from a plurality of data sources;
    aggregating the patient health data acquired from the plurality of data sources into a database;
    de-identifying the patient health data in the database; and
    training the machine learning algorithm to make medical condition state determinations, using the database and the at least one labeled biological image.

B1.1. The method of paragraph B1, wherein the labeling the at least one in situ biological image comprises labeling a plurality of in situ biological images.

B2. The method of paragraph B1.1, wherein the labeling the plurality of in situ biological images comprises manual labeling.

B3. The method of any of paragraphs B1.1-B2, wherein the labeling the plurality of in situ biological images comprises semi-supervised labeling.

B3.1. The method of any of paragraphs B1.1-B3, wherein the labeling the plurality of in situ biological images comprises manual labeling, followed by semi-supervised labeling.

B3.2. The method of any of paragraphs B1-B3.1, further comprising performing auto-labeling, wherein the performing auto-labeling is performed by the machine learning algorithm.

B4. The method of any of paragraphs B1.1-B3.2, further comprising assigning a sequential image index to each biological image of the plurality of in situ biological images.

B4.1. The method of any of paragraphs B1-B4, wherein the database comprises a text-based database.

B5. The method of any of paragraphs B1-B4.1, wherein the training the machine learning algorithm comprises a plurality of training phases.

B6. The method of paragraph B5, wherein the plurality of training phases comprises a first phase wherein the labeling is performed based on visual interpretations of each respective biological image of the at least one in situ biological image.

B7. The method of paragraph B5 or B6, wherein the plurality of training phases comprises a second phase wherein the labeling is performed based on respective pathology results for a respective biological specimen shown in a respective in situ biological image of the at least one in situ biological image.

B8. The method of any of paragraphs B1-B7, further comprising acquiring pathology results for the one or more biological specimens.

B8.1. The method of any of paragraphs B1-B8, further comprising analyzing the at least one biological specimen to determine any present medical condition state.

B9. The method of any of paragraphs B5-B.18, wherein a/the plurality of training phases comprises a third phase wherein the labeling is performed based on respective pathology results for the respective biological specimen shown in the respective in situ biological image, in combination with bounding boxes to identify an area of interest within the respective in situ biological image.

B10. The method of any of paragraphs B5-B9, wherein a/the plurality of training phases comprises a fourth phase wherein the labeling is performed based on respective pathology results for the respective biological specimen shown in the respective in situ biological image, in combination with the bounding boxes to identify the area of interest within the respective in situ biological image, and wherein the labeling is further based on the patient health data for the patient.

B11. The method of any of paragraphs B5-1310, wherein each phase of the plurality of training phases is implemented serially to train the machine learning algorithm.

B12. The method of any of paragraphs B5-B11, further comprising obtaining a respective dataset for each respective phase of the plurality of training phases, such that the method comprises using a different respective dataset for each respective phase of the plurality of training phases.

B13. The method of any of paragraphs B1-B12, wherein each biological image of the at least one in situ biological images is at least 578×462 pixels.

B14. The method of any of paragraphs B1-B13, wherein each biological image of the at least one in situ biological images is at least 720×486 pixels.

B15. The method of any of paragraphs B1-B14, wherein the training comprises training the machine learning algorithm to classify, detect, and/or localize one or more medical condition states in new biological images obtained from new patients.

B16. The method of any of paragraphs B1-B15, further comprising obtaining a plurality of medical reports for training the machine learning algorithm.

B17. The method of paragraph B16, further comprising extracting data from the plurality of medical reports, wherein the extracting data comprises extracting images and extracting text data.

B18. The method of paragraph B16 or B17, further comprising performing automated data de-identification of data extracted from the plurality of medical reports.

B19. The method of paragraph B18, wherein the performing automated data de-identification comprises assigning UUIDs, eliminating features, computed age determination, and/or generating a master database and a corresponding de-identified database.

B20. The method of any of paragraphs B1-B19, further comprising automated feature elimination of features determined to be unnecessary by the machine learning algorithm, wherein the automated feature elimination is performed by the machine learning algorithm.

B21. The method of any of paragraphs B1-B20, wherein the machine learning algorithm comprises a convolutional neural network.

C1. A method of training and preparing a machine learning algorithm for medical condition state determination, the method comprising:
    receiving an image input via at least one processing unit, wherein the image input comprises one or more images from an imaging device, and wherein the at least one processing unit comprises the machine learning algorithm stored in one or more memories of the at least one processing unit;

receiving patient health data as input, wherein the receiving patient health data is performed by the at least one processing unit; and encoding the patient health data and thereby converting the patient health data to encoded patient health data, wherein the encoding the patient health data and the converting the patient health data is performed by the at least one processing unit, wherein the machine learning algorithm is configured to make a medical condition state determination based on the image input and the encoded patient health data.

C1.1. The method of paragraph C1, further comprising adding the encoded patient health data to at least one image of the image input, wherein the adding the encoded patient health data is performed by the at least one processing unit.

C1.2. The method of paragraph C1.1, wherein the adding the encoded patient health data comprises embedding the encoded patient health data into the at least one image of the image input.

C1.3. The method of paragraphs C1.1-C1.2, wherein the adding the encoded patient health data comprises embedding the encoded patient health data into a tensor of the machine learning algorithm.

C2. The method of any of paragraphs C1-C1.2, further comprising the method of any of paragraphs B1-B21.

C3. The method of any of paragraphs C1-C2, further comprising embedding the encoded patient health data into the at least one image of the image input at or before a time that the machine learning algorithm analyzes the image input, such that the machine learning algorithm analyzes the image input together with the encoded patient health data embedded in the at least one image of the image input.

C3.1. The method of any of paragraphs C1-C3, further comprising embedding dynamic state information into the at least one image of the image input at or before a time that the machine learning algorithm analyzes the image input, such that the machine learning algorithm analyzes the image input together with the dynamic state information embedded in the at least one image of the image input.

C3.2. The method of any of paragraphs C1-C3.1, further comprising embedding the encoded patient health data into the at least one image of the image input before the receiving the image input via the at least one processing unit.

C3.3. The method of any of paragraphs C1-C3.1, further comprising embedding dynamic state information into the at least one image of the image input before the receiving the image input via the at least one processing unit.

C4. The method of any of paragraphs C1-C3.3, wherein the machine learning algorithm comprises a convolutional neural network.

C4.1. The method of any of paragraphs C1-C3.3, wherein the machine learning algorithm comprises a fully trained convolutional neural network.

C5. The method of any of paragraphs C1-C4.1, wherein the machine learning algorithm comprises a transfer learning convolutional neural network.

C6. The method of any of paragraphs C1-05, wherein the encoding the patient health data comprises performing one-hot encoding conversion.

C6.1. The method of any of paragraphs C1-C6, wherein the encoding the patient health data comprises performing data dictionary encoding.

C6.2. The method of any of paragraphs C1-C6.1, further comprising encoding dynamic state information via one-hot encoding conversion.

C6.3. The method of any of paragraphs C1-C6.2, further comprising encoding dynamic state information via data dictionary encoding.

C7. The method of any of paragraphs C1-C6.3, further comprising image encoding the encoded patient health data, wherein the image encoding is performed by the at least one processing unit, and wherein the image encoding is performed after the encoding the patient health data.

C7.1. The method of paragraph C7, wherein the image encoding comprises adding, overlaying, and/or appending image pixels to the image input.

C7.2. The method of any of paragraphs C1-C7.1, further comprising image encoding the dynamic state information, wherein the image encoding is performed by the at least one processing unit, and wherein the image encoding is performed after encoding the dynamic state information.

C7.3. The method of paragraph C7.2, wherein the image encoding comprises adding, overlaying, and/or appending image pixels to the image input.

C8. The method of any of paragraphs C1-C7.3, further comprising performing a flattening operation to flatten the encoded patient health data and/or the at least one image, wherein the performing the flattening operation is performed by the at least one processing unit.

C8.1. The method of paragraph C8, wherein the performing the flattening operation further comprises flattening the encoded dynamic state information.

C8.2. The method of any of paragraphs C1-C8.1, further comprising performing a concatenating operation to concatenate the encoded patient health data and/or the at least one image, wherein the performing the concatenating operation is performed by the at least one processing unit.

C8.3. The method of paragraph C8.2, wherein the performing the concatenating operation further comprises concatenating the encoded dynamic state information.

C8.4. The method of paragraph C8.2 or C8.3, wherein the performing the concatenating is performed prior to or within a multi-layer perceptron portion of the machine learning algorithm.

C9. The method of any of paragraphs C1-C8.4, further comprising displaying the encoded patient health data within a consistent region of an output image, wherein the displaying is performed by the at least one processing unit.

C9.1. The method of paragraph C9, wherein the displaying the encoded patient health data comprises displaying the encoded patient health data via labels and/or icons.

C9.2. The method of paragraph C9 or C9.1, wherein the displaying the encoded patient health data comprises displaying real time patient health history data to a user.

C10. The method of any of paragraphs C1-C9.2, comprising adding the encoded patient health data, wherein the adding the encoded patient health data comprises embedding the encoded patient health data within a/the consistent region of the at least one image.

C11. The method of any of paragraphs C1-C10, wherein the encoding the patient health data comprises converting the patient health data to a plurality of collections of coded image pixels that are added to, appended to, overlaid on, and/or embedded in the at least one image of the image input.

C12. The method of any of paragraphs C1-C11, further comprising adding, appending, and/or overlaying the encoded patient health data to the image input as a vector and/or a data tensor, wherein the adding, appending, and/or overlaying is performed by the at least one processing unit.

C12.1. The method of any of paragraphs C1-C12, further comprising adding, appending, and/or overlaying encoded dynamic state information to the image input as a/the vector and/or a/the data tensor, wherein the adding, appending, and/or overlaying is performed by the at least one processing unit.

C12.2. The method of any of paragraphs C1-C12.1, further comprising adding, appending, and/or overlaying the encoded patient health data to a data tensor, wherein the adding, appending, and/or overlaying is performed by the at least one processing unit.

C13. The method of paragraph C12 or C12.1, wherein the adding, appending, and/or overlaying the encoded patient health data and/or the encoded dynamic state information is performed after flattening and/or concatenating the image input and/or the encoded patient health data.

C14. The method of any of paragraphs C1-C13, wherein the encoding the patient health data comprises selectively representing the patient health data and/or dynamic state information as a/the tensor and/or a/the plurality of collections of coded image pixels.

C15. The method of any of paragraphs C1-C14, further comprising inputting the encoded patient health data into a fully connected network portion of the machine learning algorithm.

C15.1. The method of any of paragraphs C1-C15, further comprising inputting encoded dynamic state information into a/the fully connected network portion of the machine learning algorithm.

C16. The method of any of paragraphs C1-C15.1, wherein the making the medical condition state determination is performed in real-time.

C16.1. The method of any of paragraphs C1-C16, wherein the making the medical condition state determination is automated.

C17. The method of any of paragraphs C1-C16.1, further comprising:
collecting and/or retrieving the patient health data; and
delivering the patient health data to the at least one processing unit.

C18. The method of paragraph C17, wherein the collecting and/or retrieving the patient health data is performed in real-time.

C18.1. The method of any of paragraphs C1-C18, wherein the patient health data is collected or provided before the receiving the image input.

C19. The method of any of paragraphs C1-C18.1, wherein the patient health data comprises survey question answers, static data, electronic health records, electronic medical records, demographic information, medications, drug use, smoking history, computed risk predictors, blood work, prior procedural results, and/or risk factors.

C19.1. The method of any of paragraphs C1-C19, wherein the patient health data comprises body mass index (BMI), physical activity, cigarette smoking history, alcohol usage, family history, presence of inflammatory bowel disease, current hormone therapy (e.g., postmenopausal hormone therapy), former hormone therapy (e.g., postmenopausal hormone therapy), aspirin usage, nonsteroidal anti-inflammatory drugs (NSAIDs) usage, consumption of processed and/or red meat, fruit and vegetable consumption levels, demographic information, medications, drug usage, diet type and quality, dietary fat intake, weight, height, age, race, presence of other illnesses, biological markers, INR/PTT/PT/platelets/bleed time, previous endoscopy results, previous CT scan results, previous angiogram information, previous MRI results, and/or previous sonography data.

C20. The method of any of paragraphs C1-C19, wherein the making the medical condition state determination comprises detecting a medical condition state based on the one or more images and the patient health data.

C20.1. The method of paragraph C20, further comprising displaying the medical condition state.

C20.2. The method of any of paragraphs C1-C20.1, further comprising displaying the patient health data.

C21. The method of any of paragraphs C1-C20.2, wherein the making the medical condition state determination comprises classifying the medical condition state based on the one or more images and the patient health data.

C22. The method of any of paragraphs C1-C21, wherein the making the medical condition state determination comprises localizing one or more medical condition states based on the one or more images and the patient health data.

C23. The method of any of paragraphs C1-C22, further comprising de-identifying the patient health data, wherein the de-identifying the patient health data is performed by the at least one processing unit.

C24. The method of any of paragraphs C1-C23, further comprising receiving manual labeling information for the image input, wherein the receiving the manual labeling information is performed by the at least one processing unit.

C25. The method of any of paragraphs C1-C24, further comprising receiving semi-supervised labeling information for the image input, wherein the receiving the semi-supervised labeling information is performed by the at least one processing unit.

C26. The method of any of paragraphs C1-C25, further comprising performing a labeling feedback loop comprising the semi-supervised labeling information, wherein the performing the labeling feedback loop is partially performed by the at least one processing unit.

C26.1. The method of paragraph C26, wherein the performing the labeling feedback loop improves training efficiency of the machine learning algorithm.

C26.2. The method of paragraph C26 or C26.1, wherein the performing the labeling feedback loop enables training of the machine learning algorithm using large scale data and/or big data.

C27. The method of any of paragraphs C1-C26.1, wherein the machine learning algorithm comprises a custom convolutional neural network.

C28. The method of any of paragraphs C1-C27, wherein the machine learning algorithm is informed and trained using both image training data and patient health training data that is encoded such that it may be added to, appended to, overlaid on, and/or embedded in the image training data.

C29. The method of any of paragraphs C1-C28, further comprising producing an/the output image that comprises visual output for medical condition state determination that is augmented with the encoded patient health data, wherein the producing the output image is performed by the machine learning algorithm.

C29.1. The method of any of paragraphs C1-C28, further comprising producing an/the output image that comprises visual output for medical condition state determination that is augmented with the encoded patient health data, wherein the producing the output image is performed by an encoding algorithm of the at least one processing unit.

C30. The method of any of paragraphs C1-C29.1, wherein the output image comprises the at least one image of the image input and the encoded patient health data.

C31. The method of any of paragraphs C1-C30, wherein the output image further comprises the medical condition state determination determined by the machine learning algorithm.

C32. The method of any of paragraphs C1-C31, further comprising receiving dynamic state information of a patient via an apparatus, wherein the apparatus is configured to deliver the dynamic state information to the at least one processing unit as an additional input such that the receiving the dynamic state information is performed by the at least one processing unit.

C32.1 The method of paragraph C32, wherein the dynamic state information is sensor-derived data obtained in real-time during a medical imaging procedure that produces the image input.

C32.2. The method of any of paragraphs C32-C32.1, wherein the dynamic state information comprises heart rate, blood pressure, compensated heart rate, anesthetics, telemetry, saline or other fluids used, oxygen saturation, end tidal carbon dioxide (capnography), and/or activity in distal extremities.

C32.3. The method of any of paragraphs C32-C32.2, wherein the apparatus comprises one or more motion sensors, one or more accelerometers, and/or one or more video cameras configured for motion detection.

C33. The method of any of paragraphs C32-C32.3, wherein the dynamic state information comprises information regarding a patient's cardiac cycle and/or breathing cycle, and wherein the image input is temporally annotated such that each of the one or more images from the imaging device may be matched with a phase of the patient's cardiac cycle and/or breathing cycle.

C33.1. The method of any of paragraphs C32-C33, further comprising encoding the dynamic state information, wherein the encoding the dynamic state information is performed by the at least one processing unit.

C34. The method of any of paragraphs C1-C33.1, further comprising online learning performed by updating the machine learning algorithm using neural network weights, such that the machine learning algorithm continues to learn as it receives additional image input and patient health data.

C35. The method of any of paragraphs C1-C34, wherein the imaging device comprises a sonography device, an x-ray device, a computed tomography (CT) scanning device, a magnetic resonance imaging (MRI) device, a positron emission tomography (PET) device, a retinal camera, a dermatoscope, a radiograph device, a mammography device, an endoscope, a colonoscopy device, an esophagogastroduodenoscopy device, a bronchoscopy device, and/or a capsule endoscopy device.

C36. The method of any of paragraphs C1-C35, further comprising processing and interpreting the encoded patient health data, wherein the encoded patient health data is embedded in the at least one image of the image input as a/the plurality of collections of coded image pixels.

C37. The method of paragraph C36, wherein the plurality of collections of coded image pixels comprises a respective collection of coded image pixels for each respective type or category of encoded patient health data.

C38. The method of paragraph C36 or C37, wherein the collections of coded image pixels are arranged in a row, a column, and/or an array on the at least one image.

C39. The method of any of paragraphs C36-C38, wherein the collections of coded image pixels are positioned together within a given region of the at least one image.

C40. The method of any of paragraphs C3-C39, wherein a respective shade of each respective collection of coded image pixels represents a relative value of the respective encoded patient health data encoded in the respective collection of coded image pixels.

C41. The method of any of paragraphs C36-C40, wherein the plurality of collections of coded image pixels comprises a plurality of grayscale-coded image pixels.

C42. The method of any of paragraphs C36-C41, wherein the plurality of collections of coded image pixels comprises a plurality of color-coded image pixels.

C43. The method of any of paragraphs C36-C42, further comprising displaying a respective icon for each respective collection of coded image pixels in an/the output image, wherein the respective icon is configured to indicate what the respective collection of coded image pixels is encoding, wherein the displaying the respective icon is performed by the machine learning algorithm.

C43.1. The method of any of paragraphs C36-C42, further comprising displaying a respective icon for each respective collection of coded image pixels in an/the output image, wherein the respective icon is configured to indicate what the respective collection of coded image pixels is encoding, wherein the displaying the respective icon is performed by an/the encoding algorithm of the at least one processing unit.

C44. The method of any of paragraphs C1-C43.1, further comprising determining a probabilistic diagnosis of the medical condition state of the image input, based on the image input and the encoded patient health data, wherein the determining the probabilistic diagnosis is performed by the machine learning algorithm.

C45. The method of any of paragraphs C1-C44, further comprising making a/the medical condition state determination, via the machine learning algorithm, based on the image input and the encoded patient health data.

C46. The method of any of paragraphs C1-C45, further comprising producing an/the output image, via the machine learning algorithm, wherein the output image comprises the at least one image of the image input and the encoded patient health data.

C46.1. The method of any of paragraphs C1-C45, further comprising producing an output image, via an/the encoding algorithm of the at least one processing unit, wherein the output image comprises the at least one image of the image input and the encoded patient health data.

C47. The method of paragraph C46 or C46.1, wherein the output image further comprises the medical condition state determination determined by the machine learning algorithm.

C48. The method of any of paragraph C46-C47, wherein the output image further comprises current polyp count in real-time during a/the medical imaging procedure, predicted distance of travel of the imaging device within a patient's body, upcoming landmarks within the patient's body, information from previously performed medical procedures, recommendations on anesthesia, probability rates of cancer in a given area of the patient's body, a live probability of finding a polyp, a live probability of the pathology of a polyp, most recent medication the patient received, a predicated date for subsequent procedures, a predicted model of an organ of the patient being imaged, and/or summary information regarding the medical imaging procedure.

D1. A method of training and preparing a machine learning algorithm for medical condition state determination, the method comprising:
 programming at least one processing unit to receive an image input, wherein the image input comprises one or more images from an imaging device, and wherein the at least one processing unit comprises a machine learning algorithm;

programming the at least one processing unit to receive patient health data as input;

programming the at least one processing unit to encode the patient health data and thereby convert the patient health data to encoded patient health data; and programming the at least one processing unit to embed the encoded patient health data into at least one image of the image input, wherein the at least one processing unit is configured to make a medical condition state determination, via the machine learning algorithm, based on the image input and the encoded patient health data.

D2. The method of paragraph D1, comprising programming the at least one processing unit to perform the method of any of paragraphs C1-C48.

D3. The method of paragraph D1 or D2, wherein the machine learning algorithm comprises a convolutional neural network.

E1. A machine learning algorithm-implemented method for making a medical condition state determination, the method comprising:
  accessing an image input, wherein the image input comprises one or more images from an imaging device used to perform a medical imaging procedure on a patient;
  accessing patient health data;
  causing a machine learning algorithm to analyze the image input and the patient health data together to make the medical condition state determination, wherein the machine learning algorithm is configured to encode the patient health data to convert the patient health data to encoded patient health data, and wherein the machine learning algorithm is further configured to embed the encoded patient health data into at least one image of the image input; and
  accessing analysis results produced by the machine learning algorithm, wherein the analysis results comprise the medical condition state determination, and wherein the analysis results further comprise a visual representation of the encoded patient health data viewable on the analysis results.

E2. The method of paragraph E1, further comprising the method of any of paragraphs B1-B21.

E3. The method of any of paragraphs E1-E2, further comprising the method of any of paragraphs C1-C48.

E4. The method of any of paragraphs E1-E3, wherein the imaging device comprises a sonography device, an x-ray device, a computed tomography (CT) scanning device, a magnetic resonance imaging (MRI) device, a positron emission tomography (PET) device, a retinal camera, a dermatoscope, a radiograph device, a mammography device, an endoscope, a colonoscopy device, an esophagogastroduodenoscopy device, a bronchoscopy device, and/or a capsule endoscopy device.

E5. The method of any of paragraphs E1-E4, wherein the method utilizes the system of any of paragraphs A1-A39.

E6. The method of any of paragraphs E1-E5, further comprising determining dynamic state information of the patient using an apparatus, wherein the apparatus is configured to deliver the dynamic state information to the machine learning algorithm as an additional input.

E7. The method of paragraph E6, wherein the dynamic state information is sensor-derived data obtained in real-time during the medical imaging procedure.

E8. The method of paragraph E6 or E7, wherein the dynamic state information comprises information regarding a/the patient's cardiac cycle and/or breathing cycle.

E9. The method of any of paragraphs E6-E8, wherein the dynamic state information comprises information regarding a/the patient's cardiac cycle and/or breathing cycle, and wherein the image input is temporally annotated such that each of the one or more images from the imaging device may be matched with a phase of the patient's cardiac cycle and/or breathing cycle.

E10. The method of any of paragraphs E1-E9, further comprising matching the one or more images from the imaging device with cardiac cycle information of the patient, wherein the cardiac cycle information is determined dynamically during the medical imaging procedure, such that each of the one or more images from the imaging device may be matched with a phase of the patient's cardiac cycle.

E10.1. The method of any of paragraphs E1-E10, further comprising matching the one or more images from the imaging device with breathing cycle information of the patient, wherein the breathing cycle information is determined dynamically during the medical imaging procedure, such that each of the one or more images from the imaging device may be matched with a phase of the patient's breathing cycle.

E11. The method of any of paragraphs E7-E10.1, wherein the dynamic state information comprises heart rate, blood pressure, compensated heart rate, anesthetics, telemetry, saline used, other fluids used, oxygen saturation, end tidal carbon dioxide (capnography), and/or activity in distal extremities.

E12. The method of any of paragraphs E6-E11, wherein the apparatus comprises one or more motion sensors, one or more accelerometers, and/or one or more video cameras configured for motion detection.

E13. The method of any of paragraphs E1-E12, wherein the machine learning algorithm comprises a convolutional neural network.

E14. The method of any of paragraphs E1-E13, wherein the accessing the patient health data comprises collecting the patient health data in real-time.

E15. The method of any of paragraphs E1-E14, wherein the accessing the patient health data comprises retrieving the patient health data, wherein the patient health data was collected or provided before the accessing the image input.

F1. The use of the system of any of paragraphs A1-A39 to make a medical condition state determination.

As used herein, the terms "selective" and "selectively," when modifying an action, movement, configuration, or other activity of one or more components or characteristics of an apparatus, mean that the specific action, movement, configuration, or other activity is a direct or indirect result of dynamic processes and/or user manipulation of an aspect of, or one or more components of, the apparatus. The terms "selective" and "selectively" thus may characterize an activity that is a direct or indirect result of user manipulation of an aspect of, or one or more components of, the apparatus, or may characterize a process that occurs automatically, such as via the mechanisms disclosed herein.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa. Similarly, subject matter that is recited as being configured to perform a particular function may additionally or alternatively be described as being operative to perform that function.

As used herein, the phrase "at least one," in reference to a list of one or more entities should be understood to mean at least one entity selected from any one or more of the entities in the list of entities, but not necessarily including at least one of each and every entity specifically listed within the list of entities and not excluding any combinations of entities in the list of entities. This definition also allows that entities may optionally be present other than the entities specifically identified within the list of entities to which the phrase "at least one" refers, whether related or unrelated to those entities specifically identified. Thus, as a non-limiting example, "at least one of A and B" (or, equivalently, "at least one of A or B," or, equivalently "at least one of A and/or B") may refer, in one example, to at least one, optionally including more than one, A, with no B present (and optionally including entities other than B); in another example, to at least one, optionally including more than one, B, with no A present (and optionally including entities other than A); in yet another example, to at least one, optionally including more than one, A, and at least one, optionally including more than one, B (and optionally including other entities). In other words, the phrases "at least one," "one or more," and "and/or" are open-ended expressions that are both conjunctive and disjunctive in operation. For example, each of the expressions "at least one of A, B, and C," "at least one of A, B, or C," "one or more of A, B, and C," "one or more of A, B, or C" and "A, B, and/or C" may mean A alone, B alone, C alone, A and B together, A and C together, B and C together, or A, B, and C together, and optionally any of the above in combination with at least one other entity.

The various disclosed elements of apparatuses and steps of methods disclosed herein are not required to all apparatuses and methods according to the present disclosure, and the present disclosure includes all novel and non-obvious combinations and subcombinations of the various elements and steps disclosed herein. Moreover, one or more of the various elements and steps disclosed herein may define independent inventive subject matter that is separate and apart from the whole of a disclosed apparatus or method. Accordingly, such inventive subject matter is not required to be associated with the specific apparatuses and methods that are expressly disclosed herein, and such inventive subject matter may find utility in apparatuses and/or methods that are not expressly disclosed herein.

As used herein, the phrase, "for example," the phrase, "as an example," and/or simply the term "example," when used with reference to one or more components, features, details, structures, examples, and/or methods according to the present disclosure, are intended to convey that the described component, feature, detail, structure, example, and/or method is an illustrative, non-exclusive example of components, features, details, structures, examples, and/or methods according to the present disclosure. Thus, the described component, feature, detail, structure, example, and/or method is not intended to be limiting, required, or exclusive/exhaustive; and other components, features, details, structures, examples, and/or methods, including structurally and/or functionally similar and/or equivalent components, features, details, structures, examples, and/or methods, are also within the scope of the present disclosure.

The invention claimed is:

1. A method of training and preparing a machine learning algorithm for medical condition state determination, the method comprising:
    acquiring data from at least one medical procedure, wherein the acquiring data comprises acquiring at least one in situ biological image of an area of a body of a patient and acquiring one or more biological specimens from the area;
    acquiring pathology results for the one or more biological specimens;
    labeling the at least one in situ biological image based on the pathology results of the one or more biological specimens, thereby creating at least one labeled biological image that indicates respective medical condition states shown in each respective biological image;
    acquiring patient health data pertaining to the patient from a plurality of data sources;
    aggregating the patient health data acquired from the plurality of data sources into a database;
    de-identifying the patient health data in the database; and
    training the machine learning algorithm to make medical condition state determinations, using the database and the at least one labeled biological image.

2. The method according to claim 1, further comprising:
    obtaining a plurality of medical reports for training the machine learning algorithm; and
    extracting data from the plurality of medical reports, wherein the extracting data comprises extracting images and extracting text data.

3. The method according to claim 2, further comprising performing automated data de-identification of data extracted from the plurality of medical reports.

4. The method according to claim 3, further comprising automated feature elimination of features determined to be unnecessary by the machine learning algorithm, wherein the automated feature elimination is performed by the machine learning algorithm.

5. A method of training and preparing a machine learning algorithm for making a medical condition state determination, the method comprising:
    receiving an image input via at least one processing unit, wherein the image input comprises one or more images from an imaging device, and wherein the at least one processing unit comprises the machine learning algorithm stored in one or more memories of the at least one processing unit;
    receiving patient health data as input, wherein the receiving patient health data is performed by the at least one processing unit;
    encoding the patient health data and thereby converting the patient health data to encoded patient health data, wherein the encoding the patient health data is performed by the at least one processing unit, wherein the machine learning algorithm is configured to make the medical condition state determination based on the image input and the encoded patient health data; and
    embedding the encoded patient health data into at least one image of the image input at or before a time that the machine learning algorithm analyzes the image input, such that the machine learning algorithm analyzes the image input together with the encoded patient health data embedded in the at least one image of the image input.

6. The method according to claim 5, wherein the embedding the encoded patient health data into at least one image of the image input is performed before the receiving the image input via the at least one processing unit.

7. The method according to claim 5, further comprising embedding dynamic state information into at least one image of the image input, wherein the embedding dynamic state information is performed before the receiving the image input via the at least one processing unit.

8. The method according to claim 5, further comprising image encoding the encoded patient health data, wherein the image encoding and the encoding the patient health data are performed by the at least one processing unit, and wherein the image encoding and the encoding the patient health data are performed before inputting the encoded patient health data and the image input to the machine learning algorithm.

9. The method according to claim 8, wherein the image encoding comprises adding image pixels to the image input prior to the receiving the image input.

10. The method according to claim 5, further comprising:
displaying the encoded patient health data within a consistent region of an output image, wherein the displaying is performed by the at least one processing unit; and
embedding the encoded patient health data within the consistent region of the at least one image.

11. The method according to claim 10, wherein the displaying the encoded patient health data comprises displaying the encoded patient health data in real time.

12. The method according to claim 5, further comprising appending the encoded patient health data to a data tensor, wherein the appending is performed by the at least one processing unit.

13. The method according to claim 12, further comprising performing a concatenating operation to append the encoded patient health data to the data tensor, wherein the performing the concatenating operation is performed by the at least one processing unit.

14. The method according to claim 12, wherein the receiving the patient health data comprises receiving the encoded patient health data as the data tensor directly into a fully connected network portion of the machine learning algorithm, wherein the data tensor comprises both the encoded patient health data and the image input.

15. The method according to claim 5, further comprising:
one or both of: (i) collecting the patient health data in real-time and (ii) retrieving the patient health data in real-time; and
delivering the patient health data to the at least one processing unit, wherein the patient health data comprises survey question answers, static data, electronic health records, electronic medical records, demographic information, medications, drug use, smoking history, computed risk predictors, blood work, prior procedural results, and/or risk factors.

16. The method according to claim 5, further comprising performing a labeling feedback loop, wherein the performing the labeling feedback loop is partially performed by the at least one processing unit, and wherein the performing the labeling feedback look comprises:
receiving manual labeling information comprising a plurality of initial labels; and,
performing manual verification for at least a portion of the initial labels.

17. The method according to claim 5, further comprising producing an output image that comprises visual output for the medical condition state determination that is augmented with the encoded patient health data.

18. The method according to claim 5, wherein the encoding the patient health data comprises converting the patient health data to a plurality of collections of coded image pixels that are appended to or embedded in at least one image of the image input, wherein the plurality of collections of coded image pixels comprises a respective collection of coded image pixels for each respective type or category of encoded patient health data.

19. The method according to claim 18, wherein the collections of coded image pixels are arranged in a row, a column, or an array on the at least one image.

20. The method according to claim 18, wherein a respective shade of each respective collection of coded image pixels represents a relative value of the respective encoded patient health data encoded in the respective collection of coded image pixels.

21. The method according to claim 20, wherein the plurality of collections of coded image pixels comprises a plurality of grayscale-coded image pixels.

22. The method according to claim 20, wherein the plurality of collections of coded image pixels comprises a plurality of color-coded image pixels.

23. The method according to claim 18, further comprising displaying a respective icon for each respective collection of coded image pixels in an output image, wherein the respective icon is configured to indicate what the respective collection of coded image pixels is encoding.

24. The method according to claim 5, further comprising programming the at least one processing unit to produce an auditory signal when a medical condition state is detected by the machine learning algorithm.

25. The method according to claim 24, wherein the auditory signal comprises a pre-recorded sound or synthesized voice announcing the medical condition state detected by the machine learning algorithm.

26. The method according to claim 24, wherein the auditory signal comprises a pre-recorded sound or synthesized voice announcing a recommended corrective action.

27. The method according to claim 24, further comprising programming the at least one processing unit to modify a magnitude of the auditory signal, proportional to a confidence level of the machine learning algorithm associated with the medical condition state determination.

28. A method of training and preparing a machine learning algorithm for making a medical condition state determination, the method comprising:
receiving an image input via at least one processing unit, wherein the image input comprises one or more images from an imaging device, and wherein the at least one processing unit comprises the machine learning algorithm stored in one or more memories of the at least one processing unit;
receiving patient health data as input, wherein the receiving patient health data is performed by the at least one processing unit;
encoding the patient health data and thereby converting the patient health data to encoded patient health data, wherein the encoding the patient health data is performed by the at least one processing unit, wherein the machine learning algorithm is configured to make the medical condition state determination based on the image input and the encoded patient health data; and
making the medical condition state determination, via the machine learning algorithm and based on the image input and the encoded patient health data, wherein the making the medical condition state determination is performed in real-time, and wherein the making the medical condition state determination comprises one or more selected from the group comprising detecting, classifying, and localizing a medical condition state based on the one or more images and the patient health data.

29. The method according to claim 28, further comprising displaying the medical condition state determination and the encoded patient health data in real-time, via a display device.

30. A method of training and preparing a machine learning algorithm for making a medical condition state determination, the method comprising:

receiving an image input via at least one processing unit, wherein the image input comprises one or more images from an imaging device, and wherein the at least one processing unit comprises the machine learning algorithm stored in one or more memories of the at least one processing unit;

receiving patient health data as input, wherein the receiving patient health data is performed by the at least one processing unit;

encoding the patient health data and thereby converting the patient health data to encoded patient health data, wherein the encoding the patient health data is performed by the at least one processing unit, wherein the machine learning algorithm is configured to make the medical condition state determination based on the image input and the encoded patient health data; and receiving dynamic state information of a patient via an apparatus, wherein the apparatus is configured to deliver the dynamic state information to the at least one processing unit as an additional input such that the receiving the dynamic state information is performed by the at least one processing unit, wherein the dynamic state information is sensor-derived data obtained in real-time during a medical imaging procedure that produces the image input.

* * * * *